US011235093B1

(12) United States Patent
Visconti et al.

(10) Patent No.: US 11,235,093 B1
(45) Date of Patent: Feb. 1, 2022

(54) BREASTMILK COLLECTION SYSTEM

(71) Applicant: LANSINOH LABORATORIES, INC., Alexandria, VA (US)

(72) Inventors: Peter Lawrence Visconti, Gurnee, IL (US); Rush Lloyd Bartlett, II, Austin, TX (US); Yuka Yamaguchi, Arlington, VA (US); Brian T. Leadingham, Pleasant Prairie, WI (US); Patrick C. Tetzlaff, Caledonia, WI (US); Alex J. Gruber, Wind Lake, WI (US); Frank Tinghwa Wang, Taipei (TW)

(73) Assignee: Lansinoh Laboratories, Inc., Alexandria, VA (US)

( * ) Notice: Subject to any disclaimer, the term of this patent is extended or adjusted under 35 U.S.C. 154(b) by 0 days.

(21) Appl. No.: 17/182,966

(22) Filed: Feb. 23, 2021

Related U.S. Application Data

(60) Provisional application No. 63/106,132, filed on Oct. 27, 2020, provisional application No. 63/090,990, filed on Oct. 13, 2020.

(51) Int. Cl.
*A61M 1/06* (2006.01)
*A61M 1/00* (2006.01)

(52) U.S. Cl.
CPC .............. *A61M 1/064* (2014.02); *A61M 1/06* (2013.01); *A61M 1/062* (2014.02); *A61M 1/67* (2021.05); *A61M 2210/1007* (2013.01)

(58) Field of Classification Search
CPC .......... A61M 1/064; A61M 1/67; A61M 1/06; A61M 1/062; A61M 2210/1007
See application file for complete search history.

(56) References Cited

U.S. PATENT DOCUMENTS

| 8,057,425 | B1 | 11/2011 | Myers et al. |
| 8,187,227 | B2 | 5/2012 | Luzbetak et al. |
| 10,926,011 | B2 | 2/2021 | O'Toole et al. |
| 2002/0193731 | A1* | 12/2002 | Myers ............... A61M 1/062 604/74 |
| 2004/0087898 | A1* | 5/2004 | Weniger ............ A61M 1/064 604/74 |
| 2008/0171970 | A1* | 7/2008 | Luzbetak .......... A61M 1/064 604/74 |

(Continued)

FOREIGN PATENT DOCUMENTS

WO    WO2008057218 A2    5/2008

*Primary Examiner* — Amber R Stiles
(74) *Attorney, Agent, or Firm* — Merchant & Gould P.C.

(57) ABSTRACT

A breastmilk collection device includes breast contacting flange, a vacuum reservoir, flexible diaphragm separating the breast contacting flange and the vacuum reservoir, and a flange receiver between the breast contacting flange and the flexible diaphragm. The breast contacting flange has a wide portion for accepting the breast and a narrow portion. The flexible diaphragm is located between the narrow portion and the vacuum reservoir. The flexible diaphragm moves between a sealed configuration, in which the breast contacting flange is sealed off from the vacuum reservoir, and an open valve configuration, in which the flexible diaphragm acts as a one-way valve to allow expressed milk to flow through a milk flow opening between the flexible diaphragm and the breast contacting flange when an opening pressure is reached in the breast contacting flange.

23 Claims, 21 Drawing Sheets

(56) References Cited

U.S. PATENT DOCUMENTS

| | | | | |
|---|---|---|---|---|
| 2013/0023821 | A1* | 1/2013 | Khalil | A61M 1/82 |
| | | | | 604/74 |
| 2015/0335800 | A1* | 11/2015 | Yamashita | A61M 1/06 |
| | | | | 604/74 |
| 2018/0104396 | A1* | 4/2018 | Park | A61M 1/062 |
| 2018/0361040 | A1 | 12/2018 | O'Toole et al. | |

* cited by examiner

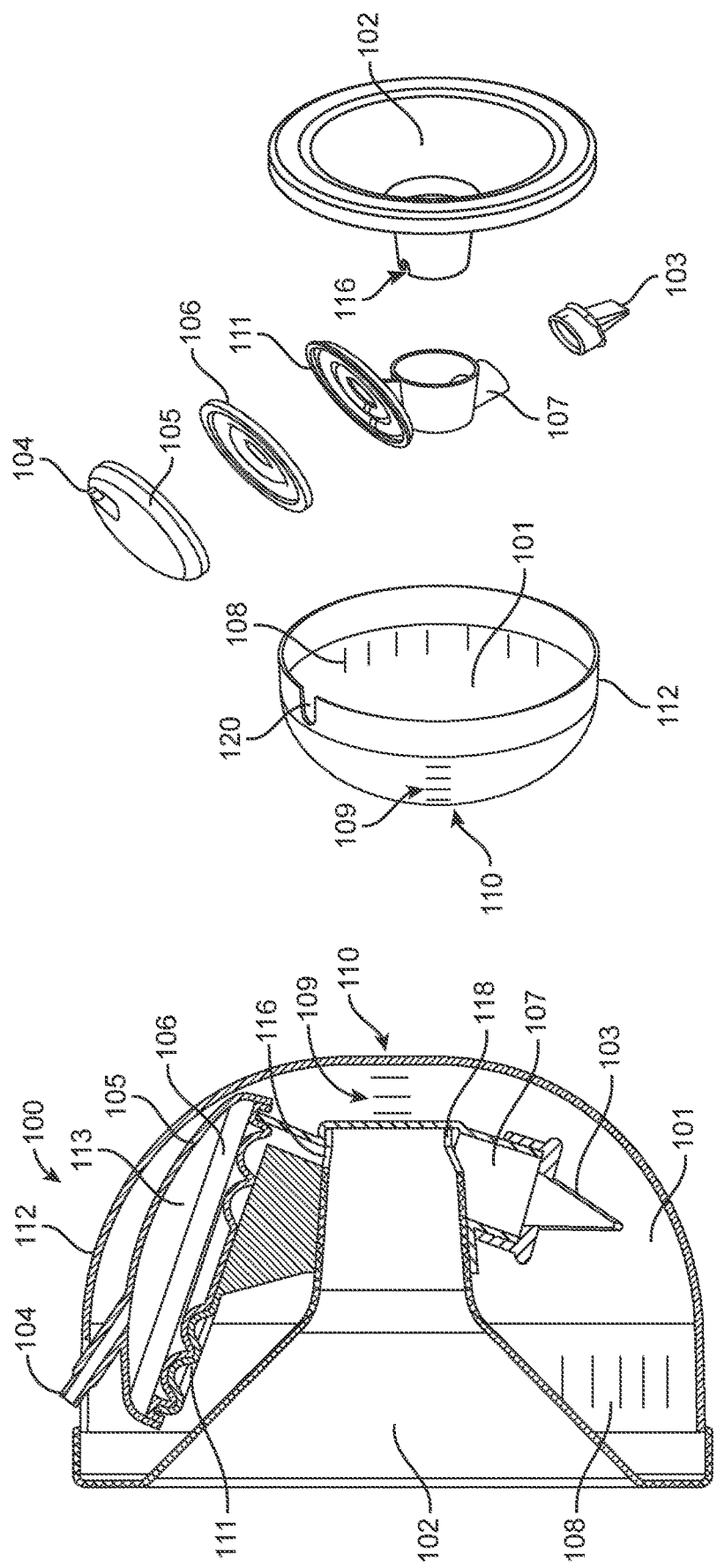

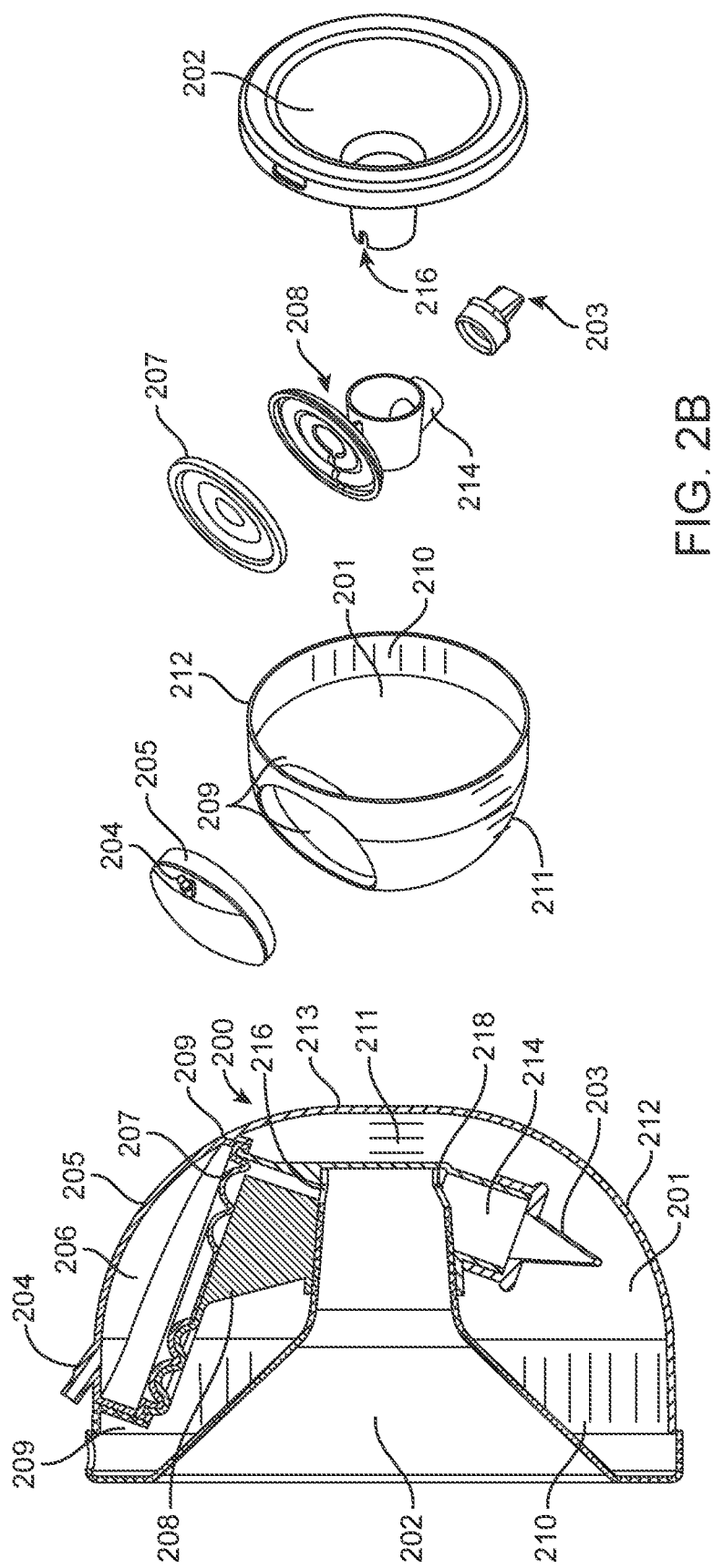

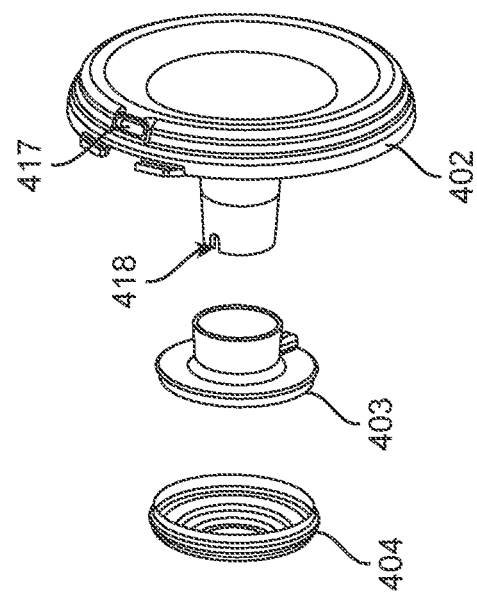
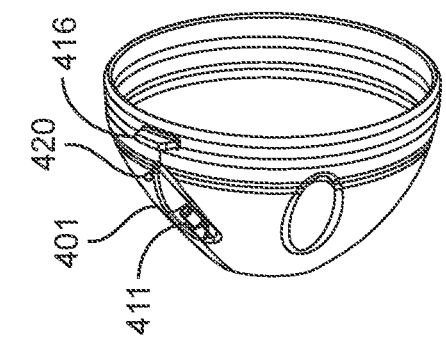
FIG. 4B
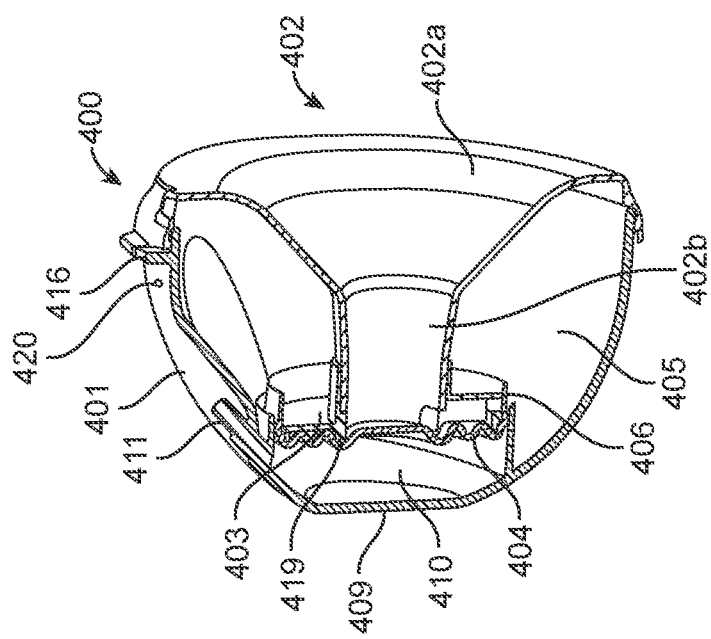
FIG. 4A

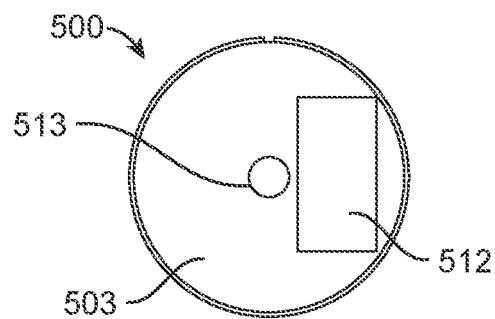
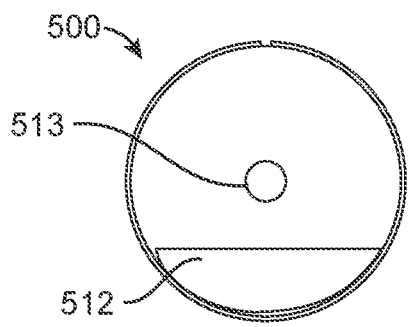
FIG. 8A　　　　　　　　FIG. 8B
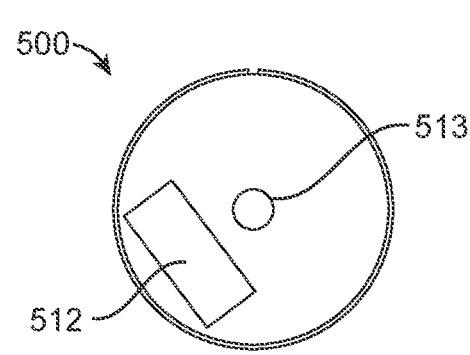
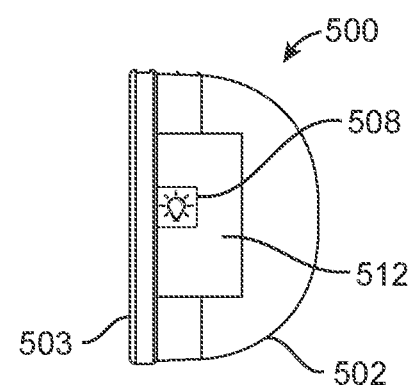
FIG. 8C　　　　　　　　FIG. 8D

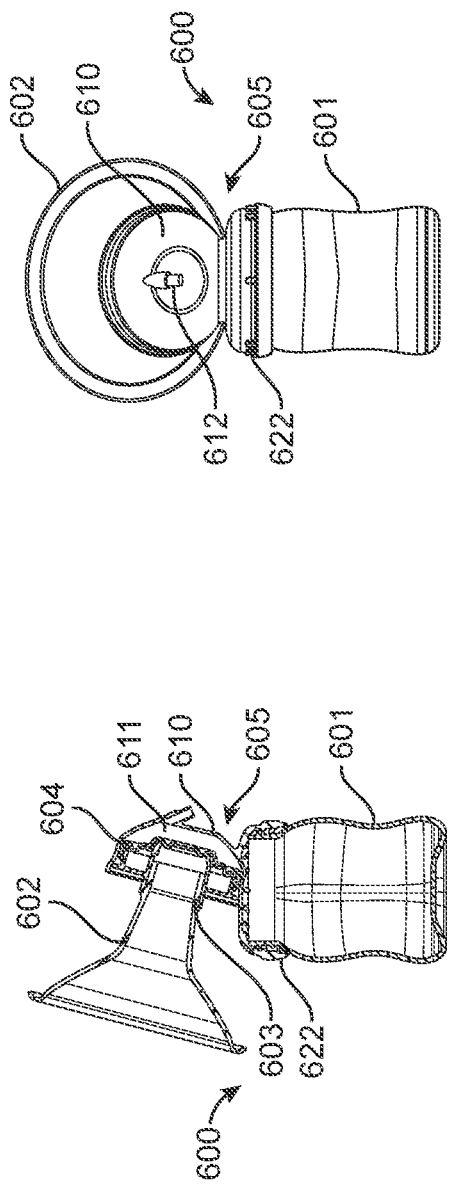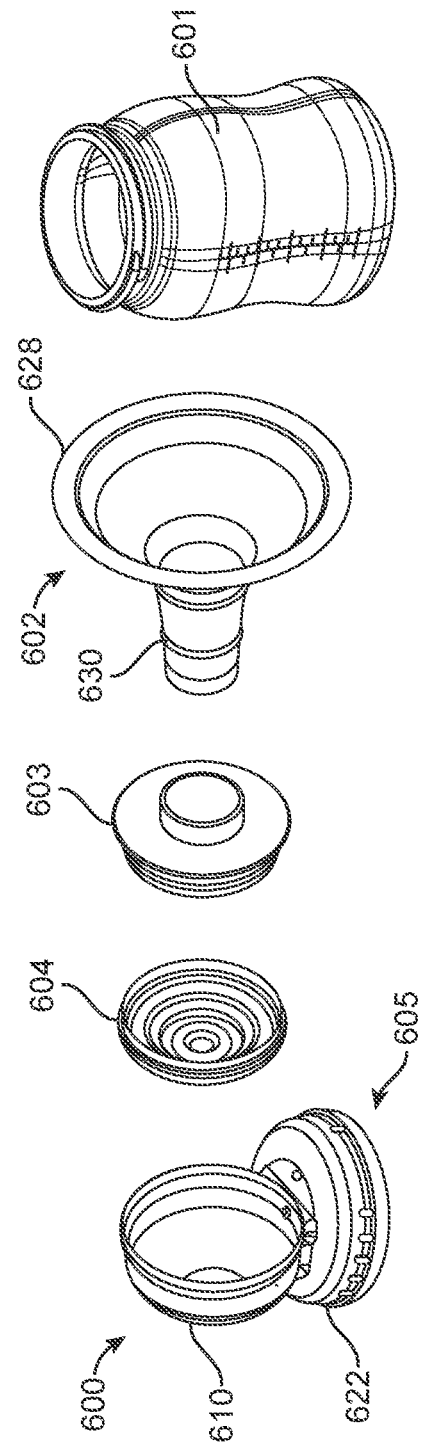

BREASTMILK COLLECTION SYSTEM

CROSS-REFERENCE TO RELATED APPLICATIONS

This application claims priority to U.S. Provisional Patent Application Serial Nos. 63/090,990, filed Oct. 13, 2020, and titled "Breastmilk Collection System," and 63/106,132, filed Oct. 27, 2020, also titled "Breastmilk Collection System." The above-referenced provisional patent applications are hereby incorporated by reference in this application.

BACKGROUND

Breastmilk contains all the nutrients a baby needs for the first six months of life to support growth and development. Therefore, breastfeeding and/or breastmilk feeding is recommended globally by the World Health Organization and healthcare professionals. When possible, mothers should be supported to initiate breastfeeding within the first hour of their baby's life, breastfeed exclusively for six months, and continue breastfeeding while giving appropriate complementary foods for up to two years of age or beyond. There are situations, however, when direct breastfeeding is not possible. For example, babies may not be able to latch and suckle, due to cleft palate or tongue tie, prematurity, low birthweight, or other causes, and mothers may not be able to breastfeed, due to medical conditions or recovery from birth trauma. In such cases, human breastmilk feeding becomes the next best option. The principle methods used by mothers to collect human breastmilk are hand expressing breastmilk into a container and expressing breastmilk using a manual or electric breast pump. For many mothers, a breast pump plays a significant role in the breastmilk feeding process. Unfortunately, breast pumps are often cumbersome, obtrusive, noisy and inconvenient to carry from place to place and use.

Breast pump discretion and mobility are poorly met needs. Traditional breast pump systems use collection kits that include breast flanges and bottles. Although effective, these systems do not support discretion, mobility or ease of use and assembly. More recent systems use pump systems and/or collection cups that fit inside a breast pumping mother's bra but include at least five components, not including tubing or a suction source. These systems tend to be difficult to use and complicated to assemble. Therefore, there is a distinct need for a breastmilk expression system that is more convenient, comfortable and unobtrusive. Ideally, such a system would facilitate emptying as much breastmilk as possible from a breast, to increase milk supply and minimize risk of breast engorgement. Also ideally, the system would be relatively easy to use, require only minimal/simple assembly, would enable a woman to express milk discretely, and would provide for easier mobility.

SUMMARY OF THE INVENTION

Regularly expressing breastmilk, whether by nursing or pumping, is a critical factor for mothers to establish and maintain breastmilk supply, even if an infant is not nursing at all or not nursing well. This disclosure describes a device and system that offers flexibility and convenience for pumping and collecting expressed breastmilk. In some embodiments, the device fits in a brassiere and is attached to an electric pump using silicone tubes for applying vacuum to the device's pump. In other embodiments, the pump is directly attached to the device. The breastmilk collection device, securely supported by a brassiere, becomes a hands-free device that enables the lactating mother to pump and/or collect expressed milk without holding the device. It also allows a woman to pump and collect expressed breastmilk from one breast while breastfeeding an infant on the other breast.

In one aspect of the present disclosure, a breastmilk collection device includes a breast contacting flange having a wide portion for accepting the breast and a narrow portion, a vacuum reservoir, a flexible diaphragm separating the narrow portion of the breast contacting flange and the vacuum reservoir, and a flange receiver coupled with the narrow portion of the breast contacting flange, between the flexible diaphragm and the breast contacting flange. The flexible diaphragm is configured to move between a sealed configuration, in which the breast contacting flange is sealed off from the vacuum reservoir, and an open valve configuration, in which the flexible diaphragm acts as a one-way valve to allow expressed milk to flow through a milk flow opening between the flexible diaphragm and the flange receiver when an opening pressure is reached in the breast contacting flange.

In some embodiments, the breastmilk collection device also includes a cup attached to the wide portion of the breast contacting flange. The cup has a first portion that forms a milk container and a second portion that forms the vacuum reservoir. The cup may also include a suction tube attachment port in fluid communication with the vacuum reservoir. Optionally, the cup may also include measurement lines to measure milk stored in the milk storage compartment. In some embodiments, the device also includes a breast pump attached to the cup. In some embodiments, the breast pump is removably attached to the cup. Alternatively, the breast pump may be located inside the storage compartment. Such an internal pump may include a printed circuit board and a power source. Some embodiments may further include tubing for connecting the breast pump to an additional wearable breastmilk collection device, such that the wearable breastmilk collection device and the additional wearable breastmilk collection device can be worn at the same time and used simultaneously or sequentially.

In some embodiments, the flexible diaphragm forms a seal with the flange receiver in the sealed configuration, and a portion of the flexible diaphragm unseals from the flange receiver to allow the expressed milk to flow out of the milk flow opening between the flexible diaphragm and the flange receiver. The flange receiver has an opening into which the narrow portion of the breast contacting flange fits for attachment, and the flexible diaphragm is attached to a side of the flange receiver that is opposite the breast contacting flange. In some embodiments, the flange receiver and the breast contacting flange are one piece.

In some embodiments, the device further includes an adapter attached to the flange receiver and/or the narrow portion of the breast contacting flange. The adapter typically forms the vacuum reservoir and houses the flexible diaphragm. The adapter may include a suction tube attachment port in fluid communication with the vacuum reservoir. The adapter may also include a milk container attachment portion for attaching to a milk container. In some embodiments, a flange connecting portion of the adapter is configured to move by tilting and/or rotating relative to the milk container attachment portion.

In manual embodiments, the device may also include a pull rod attached to the flexible diaphragm and extending out of an opening on a back of the adapter and a handle attached to the adapter and the pull rod for pulling back on the pull rod to manually pull on the flexible diaphragm to generate vacuum force. Optionally, the pull rod may have two settings defining two different locations for attachment of the handle to the pull rod, to generate at least two different amounts of pulling force on the flexible diaphragm.

In another aspect of the present disclosure, a method of expressing and collecting breastmilk from a breast involves positioning the breastmilk collection device described above on the breast and expressing breastmilk from the breast, using the breastmilk collection device. In some embodiments, positioning the breastmilk collection device on the breast involves positioning the breastmilk collection device inside of a brassiere. Such a method may further involve attaching the breastmilk collection device to a pump located outside of the brassiere. Attaching the breastmilk collection device to the pump may involve attaching tubing from the pump to a vacuum source attachment port of the breastmilk collection device that is in fluid communication with the vacuum reservoir.

Alternatively, the method may involve attaching the breastmilk collection device to a pump located inside the brassiere. In other embodiments, expressing breastmilk from the breast involves squeezing a handle of the breastmilk collection device. The method may optionally also include adjusting a position of an attachment point of the handle to a pull rod of the breastmilk collection device to change an amount of pulling force generated on the flexible diaphragm by the handle. In other embodiments, the method involves attaching the breastmilk collection device to an electric pump to express the breastmilk. The method may also involve attaching a milk container to the breastmilk collection device to collect the expressed breastmilk.

In one aspect of the present disclosure, a wearable breastmilk collection device includes a cup and a breast contacting flange attached to the cup, where an inner space formed by the attached cup and breast contacting flange serves as a milk storage compartment. The breast contacting flange may include a first opening for allowing vacuum force to enter the breast contacting flange and a second opening for allowing expressed milk to exit the breast contacting flange. The device also includes flexible diaphragm in the vacuum reservoir, where vacuum force generated by the flexible diaphragm is transmitted into the breast contacting flange via the first opening, and a one-way valve located between the second opening on the breast contacting flange and the milk storage compartment.

In some embodiments, the vacuum reservoir has a dome shape or a half-dome shape. In some embodiments, the vacuum reservoir is housed completely within the milk storage compartment, while in others the vacuum reservoir protrudes out of the cup or a portion of the cup forms a wall of the vacuum reservoir. In some embodiments, the device also includes a vacuum source attachment port in fluid communication with the vacuum reservoir for attaching with tubing from an external breast pump.

Optionally, the device may include a flange receiver attached to the vacuum reservoir, the one-way valve and the breast contacting flange. The flange receiver may include a lower vacuum communication wall leading to the first opening of the breast contacting flange. In some embodiment, the one-way valve is formed by a contact point between the flange receiver ad the flexible diaphragm. Alternatively, the one-way valve may be a duck-bill valve or any other suitable form of one-way valve. In some embodiments, the cup may include measurement lines to measure milk stored in the milk storage compartment.

Some embodiments further include a breast pump attached to the cup. The breast pump may be removably attached to the cup. The breast pump may be located inside the storage compartment and may include a printed circuit board and a power source. Some embodiments may include tubing for connecting the breast pump to an additional wearable breastmilk collection device, such that the wearable breastmilk collection device and the additional wearable breastmilk collection device can be worn at the same time and used simultaneously or sequentially.

In another aspect of the present disclosure, a breastmilk collection device includes a breast contacting flange, a milk container, an adapter comprising a flange connecting portion and a milk container connecting portion, a flexible diaphragm in the adapter, a vacuum source attachment port on the adapter, and a reservoir between the flexible diaphragm and the vacuum source attachment port. Vacuum force is transmitted through the vacuum source attachment port and the vacuum reservoir to move the flexible diaphragm and thus generate vacuum force in the breast contacting flange.

In some embodiments, the milk container is a bottle. Some embodiments may include a flange receiver in the adapter, attached on one side to the flexible diaphragm and on an opposite side the breast contacting flange. In some embodiments, the flange connecting portion of the adapter is configured to tilt relative to the milk container connecting portion. In some embodiments, the flange connecting portion of the adapter is configured to rotate relative to the milk container connecting portion.

In another aspect of the present disclosure, a breastmilk collection device includes a breast contacting flange, a milk container, an adapter comprising a flange connecting portion and a milk container connecting portion, a flexible diaphragm in the adapter, a pull rod attached to the diaphragm, and a handle attached to the adapter and the pull rod for pulling back on the pull rod to manually pull on the flexible diaphragm to generate vacuum force. Vacuum force generated by the flexible diaphragm is transmitted into the breast contacting flange. Optionally, the pull rod may include two bulbs, and herein the handle is adjustable in its attachment to the pull rod to be located in at least two different locations relative to the two bulbs, to generate at least two different amounts of pulling force on the flexible diaphragm. The device may include a flange receiver in the adapter, attached on one side to the flexible diaphragm and on an opposite side the breast contacting flange.

In another aspect of the present disclosure, a method of expressing and collecting breastmilk from a breast involves positioning a wearable breastmilk collection device on the breast, inside of a brassiere, and expressing breastmilk from the breast, using the wearable breastmilk collection device. The wearable breastmilk collection device may have any of the components and features described above. In some embodiments, the method involves attaching the wearable breastmilk collection device to a pump located outside of the brassiere. In other embodiments, the method involves attaching tubing from the pump to a vacuum source attachment port of the wearable breastmilk collection device that is in fluid communication with the vacuum reservoir. The method may also involve attaching the wearable breastmilk collection device to a pump located inside the brassiere.

In another aspect of the present disclosure, a method of expressing and collecting breastmilk from a breast involves positioning a manual breastmilk collection device on the breast and using a handle of the device to express breastmilk from the breast. The manual breastmilk collection device includes a breast contacting flange, a milk container, an adapter comprising a flange connecting portion and a milk container connecting portion, a flexible diaphragm in the adapter, a pull rod attached to the diaphragm, and a handle attached to the adapter and the pull rod for pulling back on the pull rod to manually pull on the flexible diaphragm to generate vacuum force.

In some embodiments, the method further involves adjusting a position of an attachment point of the handle to the pull rod to change an amount of pulling force generated on the flexible diaphragm by the handle. The method may also involve noting an amount of milk in the milk container by viewing a fluid level of the milk relative to fluid level measurement lines on the milk container and removing the milk container from the adapter. Using the handle may involve compressing the handle with the handle in a first attachment position relative to the pull rod to stimulate the breast and compressing the handle with the handle in a second attachment position relative to the pull rod to express milk from the breast.

According to various embodiments, the breastmilk collection system described herein includes a breast contacting flange, a flange receiver, and a flexible diaphragm and a breastmilk collection container that uses electric vacuum power source for pumping. The opening side of a funnel shaped breast flange that is applied to the breast may be formed as a lid to a cup shaped collection container to secure collected expressed breastmilk inside the container. A funnel shaped breast flange is inserted into a flange receiver and assembled with a valve to let expressed human breastmilk drip into the collection container. A breast flange tunnel can be narrower or wider to work with different sizes of nipples. Some embodiments may include a check valve integration of a flange receiver and a valve to minimize the risk of improper assembly and misuse. A check valve allows reduction of a number of parts for convenience and to make a collection device compact.

These and other aspects and embodiments are described in further detail below, in reference to the attached drawing figures.

BRIEF DESCRIPTION OF THE DRAWINGS

FIG. 1A is a side, cross-sectional view of a breastmilk collection device, according to one embodiment;

FIG. 1B is an exploded view of the breastmilk collection device of FIG. 1A;

FIG. 2A is a side, cross-sectional view of a breastmilk collection device, according to an alternative embodiment;

FIG. 2B is an exploded view of the breastmilk collection device of FIG. 2A;

FIG. 4A is a side/perspective, cross-sectional view of a breastmilk collection device, according to an alternative embodiment;

FIG. 4B is an exploded view of the breastmilk collection device of FIG. 4A;

FIGS. 8A-8C are rear views of three alternative embodiments of a breastmilk collection device with an internal electric pump, where the pump is located in different positions;

FIG. 8D is a side view of a breastmilk collection device with an electric pump, illustrating operation of an optional light;

FIGS. 9A-9C are side/cross-sectional, rear and exploded views, respectively, of a breastmilk collection device with a removable milk containment device, according to another alternative embodiment;

DETAILED DESCRIPTION

Figure 3B:
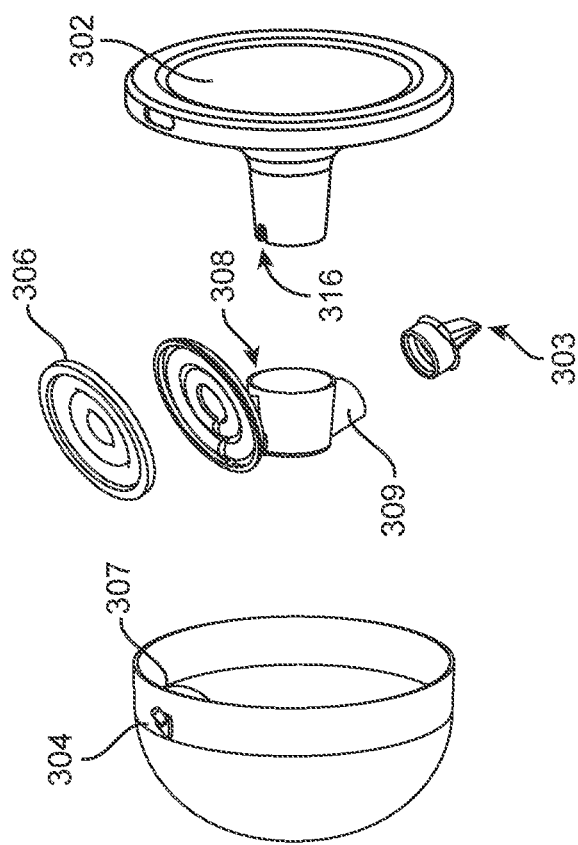
FIG. 3B is an exploded view of the breastmilk collection device of FIG. 3A.

Embodiments described herein include both wearable breast pump devices and portable devices that are not wearable. Each embodiment includes one or more new and improved components or features, as compared to currently available breast pumps, to facilitate wearability, portability and/or breast milk expression and collection.

FIGS. 1A and 1B illustrate one embodiment of a wearable breastmilk collection device 100 that is worn within a woman's brassier while collecting milk. FIG. 1A is a side, cross-sectional view, and FIG. 1B is an exploded view. As with all of the embodiments described herein, the collection device 100 may be used as part of any breast pump system, and it is not limited to use with any particular system.

In this embodiment, the wearable breastmilk collection device 100 includes a milk storage compartment 101 that is formed by a breast contacting flange 102 coupled with a cup 112 and is separated from the breast contacting flange 102 by a one-way valve 103, such as but not limited to a duckbill valve. The collection device 100 is operated under variable suction parameters of vacuum through an external vacuum source attachment port 104 that provides suction to an vacuum reservoir 113 formed by a half dome 105 attached to a flexible diaphragm 106. The vacuum reservoir 113 is created by compressing the half dome 105 against the flexible diaphragm 106 and a flange receiver 111, which includes a lower vacuum communication wall with an outlet into an upper opening 116 on the breast contacting flange 102. Communication of suction force from the vacuum reservoir 113 to the breast contacting flange 102 is achieved through the flexible diaphragm 106. Vacuum force is actuated from the flexible diaphragm 106 in cycles, which helps to extract milk or colostrum from the breast. Milk flows from the breast through a lower opening 118 on the breast contacting flange 102 and into a collection compartment 107 anterior to the one-way valve 103. The wearable breastmilk collection device 100 may optionally include horizontal 108 and/or vertical 109 measurement lines, to help the user determine the volume of fluid contained within the wearable breastmilk collection device 100 if the cup 112 was in place on the breast vertically or placed on the table in the prone position with a flat resting edge 110 touching the table.

FIG. 1B shows the components of the wearable breastmilk collection device 100 in exploded view. Again, the cup 112 attaches to the breast contacting flange 102 to form the storage compartment 101. The wide open end of the breast contacting flange 102 is configured to accept the woman's breast for milk collection. The flange receiver 111 and the collection compartment 107 may be one piece, with the diaphragm 106 fitting into the flange receiver 111 and the one-way valve 103 fitting onto the end of the collection compartment 107. The half dome 105 with its vacuum source attachment port 104 fits on top of and over the edges of the flange receiver 111 and the diaphragm 106. The vacuum source attachment port 104 extends through an opening 120 on the top of the cup 112, when the collection device 100 is assembled. All the parts of the collection device 100 may be made of any suitable material or combination of materials. For example, some or all of the parts may be made of one or more plastics. The diaphragm 106 may be made of a flexible rubber material. The breast contacting flange 102 may be made out of a polymer designed to interact comfortably with the woman's breast. Again, any suitable materials may be used in the construction of the collection device 100. The various parts may be attached to one another using glue, other adhesive material, press fit, snap fit or any other suitable attachment mechanism(s).

In use, the breast contacting flange 102 is placed over the woman's breast. Suction tubing (not illustrated) is attached to a breast pump (not illustrated) at one end and to the vacuum source attachment port 104 at an opposite end.

When the breast pump is activated, suction force is transmitted from the breast pump through the suction tubing to the vacuum source attachment port 104 and thus into the vacuum reservoir 113. This suction force pulls up on the diaphragm 106 and thus transmits suction force via the upper opening 116 into the interior, breast contacting portion of the breast contacting flange 102. This suction force helps express milk from the breast. Expressed milk travels through the lower opening 118 on the breast contacting flange 102 and into the collection compartment 107 and then through the one-way valve 103 and into the storage compartment 101. Back pressure in the collection device 100, along with gravity, helps pull the expressed milk through the one-way valve 103.

FIGS. 2A and 2B illustrate an alternative embodiment of a wearable breastmilk collection device 200. FIG. 2A is a side, cross-sectional view, and FIG. 2B is an exploded view. The wearable breastmilk collection device 200 includes a storage compartment 201 formed by the coupling of a breast contacting flange 202 with a cup 212. The cup 212 is separated from the breast contacting flange 202 by a one-way valve 203, such as but not limited to a duckbill valve. The collection device 200 is operated under variable suction parameters of vacuum through an external vacuum source attachment port 204 positioned on a half dome 205, to provide suction to an vacuum reservoir 206. The vacuum reservoir 206 is formed by compressing the half dome 205 against a flexible diaphragm 207 and is securely locked by a receptacle 209 of the cup 212 to form a complete seal to store expressed breastmilk. Below the flexible diaphragm 207 is a flange receiver 208 that has a lower vacuum communication wall with an outlet into an upper opening 216 on the breast contacting flange 202. Communication of suction force from the vacuum reservoir 206 to the breast contacting flange 202 is achieved through the flexible diaphragm 207. Vacuum force is actuated from the flexible diaphragm 207 in cycles, which helps to extract milk or colostrum from the breast and allow it to flow through a lower opening 218 the breast contacting flange 202 into a collection compartment 214 anterior to the one-way valve 203. The wearable breastmilk collection device 200 may optionally include horizontal 210 and/or vertical 211 measurement lines to help the user determine the volume of fluid contained within the wearable breastmilk collection device 200 if the cup 212 was in place on the breast vertically or placed on the table in the prone position with a flat resting edge 213 touching the table. Any of the features and details described above in relation to one or more different embodiments may also be applied to this embodiment.

Figure 3A:
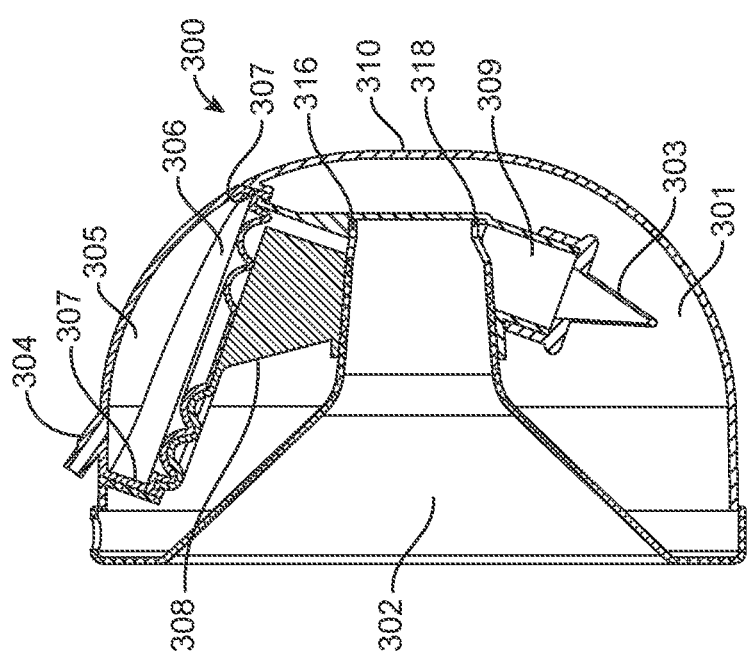
FIG. 3A is a side, cross-sectional view of a breastmilk collection device, according to an alternative embodiment.

FIGS. 3A and 3B illustrate another alternative embodiment of a wearable breastmilk collection device 300. FIG. 3A is a side, cross-sectional view, and FIG. 3B is an exploded view. The wearable breastmilk collection device 300 includes a storage compartment 301 formed by the coupling of a breast contacting flange 302 and a cup 310. The storage compartment 301 and separated from a breast contacting flange 302 by a one-way valve 303, such as but not limited to a duckbill valve. The collection device 300 is operated under variable suction parameters of vacuum through an external vacuum source attachment port 304 on the cup 310 that provides suction to an vacuum reservoir 305. The vacuum reservoir 305 is formed by attachment of the cup 310 to the flexible diaphragm 306, which in turn is securely locked into a receptacle 307, which is also part of the cup 310 and thus has one fewer component than the previously described embodiment. A flange receiver 308 includes a lower vacuum communication wall with outlet into the opening of the breast contacting flange 302. Communication of the suction force from the vacuum reservoir 305 to the breast contacting flange 302 is achieved through the flexible diaphragm 306 and through an upper opening 316 on the breast contacting flange 302. Vacuum force is actuated from the flexible diaphragm 306 in cycles, which helps extract milk or colostrum from the breast and allow it to flow through a lower opening on the breast contacting flange 302 into a collection compartment 309 anterior to the one-way valve 303. Any of the features and details described above in relation to one or more different embodiments may also be applied to this embodiment.

FIGS. 4A and 4B illustrate another alternative embodiment of a wearable breastmilk collection device 400. FIG. 4A is a side/perspective, cross-sectional view, and FIG. 4B is an exploded view. The wearable breastmilk collection device 400 includes a collection receptacle 401 (or "cup"), a breast contacting flange 402, a flange receiver 403 and a flexible diaphragm 404 that acts as a one-way valve. The cup/collection receptacle 401 includes a vacuum source attachment port 411, which is in fluid communication with a vacuum reservoir 410. A milk storage compartment 405 that receives the expressed breastmilk is formed by the inward facing walls of the collection receptacle 401, the breast contacting flange 402 and diaphragm 404. The milk storage compartment 405 is created by coupling the breast contacting flange 402 with the collection receptacle 401 and is separated from the breast contacting flange 402 by the flexible diaphragm 404. The vacuum reservoir 410 is a separate area formed by the collection receptacle 401 behind the flexible diaphragm 404 and sealed off from the milk storage compartment 405, so that milk does not enter the vacuum reservoir. The breast contacting flange 402 has a wide portion 402a at the outward facing end, into which the woman places her breast, and tapers down to a narrow portion 402b, which attaches to the flange receiver 403.

Figure 4C:
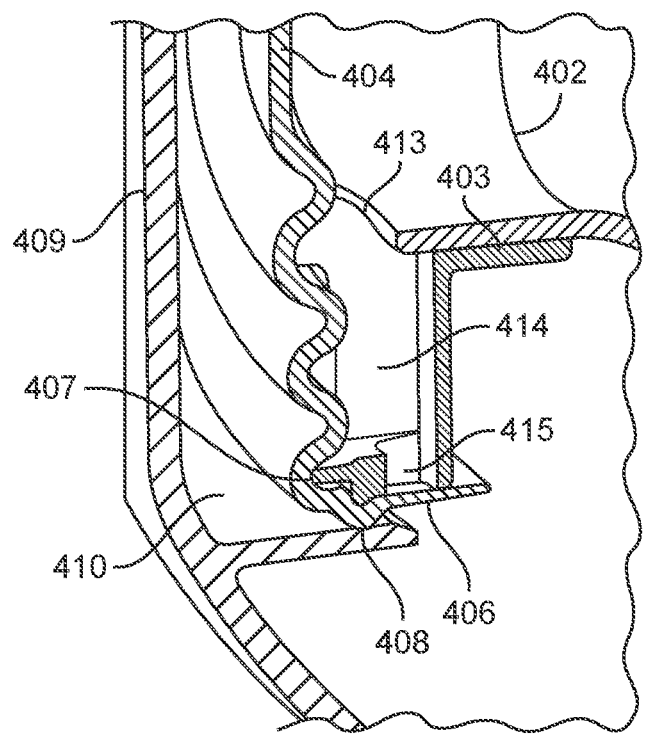
FIGS. 4C and 4D are partial cross-sectional views of the breastmilk collection device of FIGS. 4A and 4B, illustrating a path for milk flow through the device.
Figure 4D:
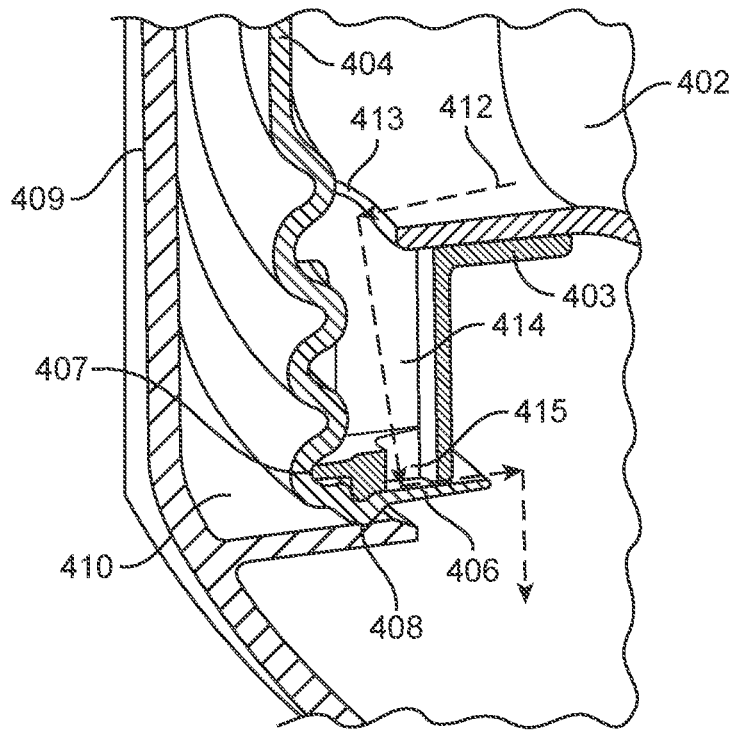
Figure 5A:
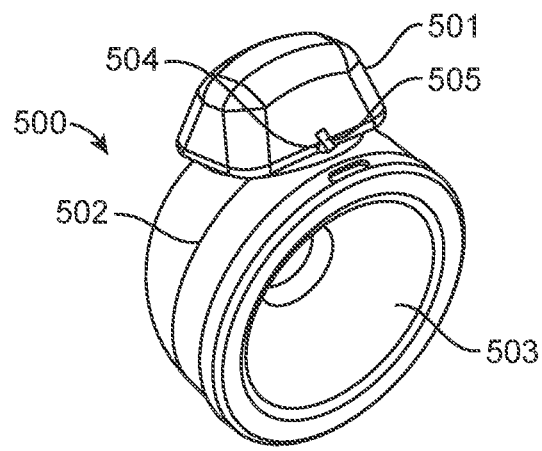
FIGS. 5A-5C are perspective, side and rear views, respectively, of a breastmilk collection device with an electric pump, according to one embodiment.
Figure 5B:
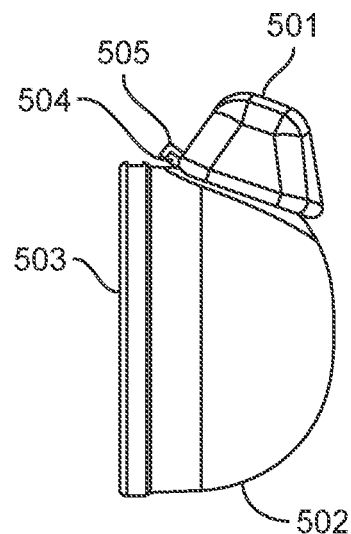
Figure 5C:
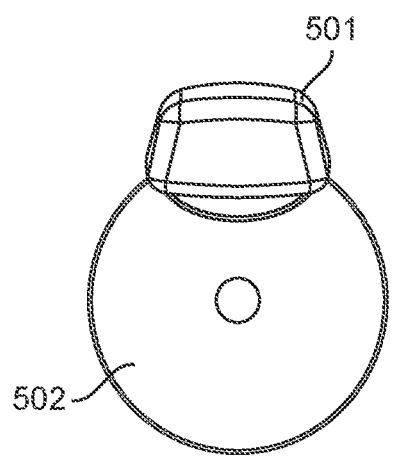
Figure 5D:
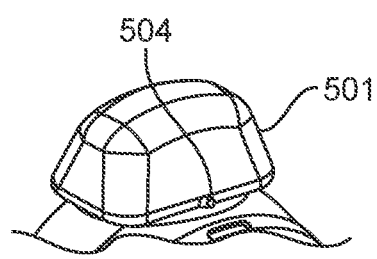
FIG. 5D is a partial perspective view of the breastmilk device of FIGS. 5A-5C, illustrating an optional light for nighttime visualization.

Referring to FIGS. 4C and 4D, the flexible diaphragm 404 includes an integrated one-way valve 406, which may be a flapper valve, as in this embodiment, or any other suitable type of valve. In some embodiments, the one-way valve 406 is an outer rim of the flexible diaphragm 404. In other embodiments, the one-way valve 406 may be a tab or other extension off of the flexible diaphragm 404. The one-way valve 406 contacts the flange receiver 403 and the collection receptacle 401 to form an inner seal 407 and outer seal 408. The flexible diaphragm 404 is captured between the flange receiver 403 and the collection receptacle 401, whose half dome top 409 forms the vacuum reservoir 410 with the flexible diaphragm 404. The vacuum reservoir 410 is created by compressing the flange receiver 403 against the flexible diaphragm 404 and the collection receptacle 401. In some embodiments, as in FIGS. 4A-4D, the one-way valve 406 is formed by contact between the flexible diaphragm 404 and the flange receiver 403. In alternative embodiments, the one-way valve 406 may be formed by contact between the flexible diaphragm 404 and the breast contacting flange 402.

The wearable breastmilk collection device 400 is operated under variable suction parameters of vacuum, applied by an electric breast pump (not illustrated), connected via suction tubing to the vacuum source attachment port 411, which provides suction to the vacuum reservoir 410. Communication of the suction force from the vacuum reservoir 410 to the breast contacting flange 402 is achieved through the flexible diaphragm 404. Vacuum force is actuated from the flexible diaphragm 404 in cycles, which helps to extract milk or colostrum from the breast and allow it to flow into the storage compartment 405 anterior to the one-way valve 406.

The flow path 412 from the breast contacting flange 402 to the storage compartment 405 includes the flow entrance 413, located at the distal end of the breast contacting flange 402, flow chamber 414 and flow exit 415. As air is pushed back into vacuum reservoir 410 and milk flows into the storage compartment 405, air is displaced and exits through a vent hole 420, which may optionally include a float restrictor or valve to prevent spillage through the vent hole 420 when a user bends over. Some systems may not need a vent hole 420, if the amount of displaced air vents around another part of the seal mechanism above the liquid level.

To ensure proper flow, an alignment mechanism is included, which aligns the breast contacting flange 402, the collection receptacle 401 and the flange receiver 403. During assembly, the flange receiver 403 is pressed onto the breast contacting flange 402, and a slot 418 on the breast contacting flange 402 accepts a post 419 on the flange receiver 403. A securing feature 416 on the collection receptacle 401 is also placed into a receiving feature 417 on the breast contacting flange 402, prior to pressing the breast contacting flange 402 onto the collection receptacle 401.

FIGS. 5A-5D illustrate another alternative embodiment of a wearable breastmilk collection device 500. The wearable breastmilk collection device 500 includes an external breast pump 501 attached to a collection receptacle 502 (or "cup"). The collection device 500 is operated under variable suction parameters of vacuum by the external breast pump 501 and is connected to an external vacuum source attachment 504 by a pump connecter 505. Using the pump connector 505 gives a pumping mother the option of using different external breast pumps.

Figure 6A:
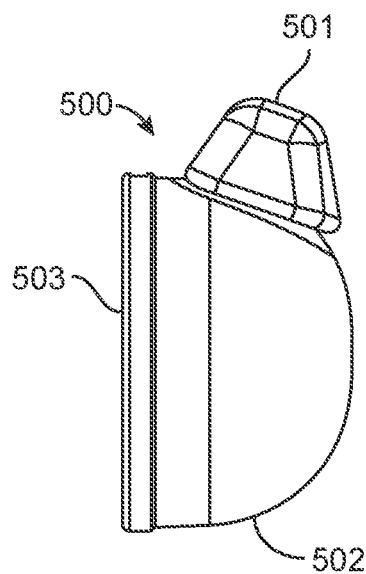
FIGS. 6A-6C are side, partial cross-section and exploded views, respectively, of a breastmilk collection device with an electric pump, according to an alternative embodiment.
Figure 6B:
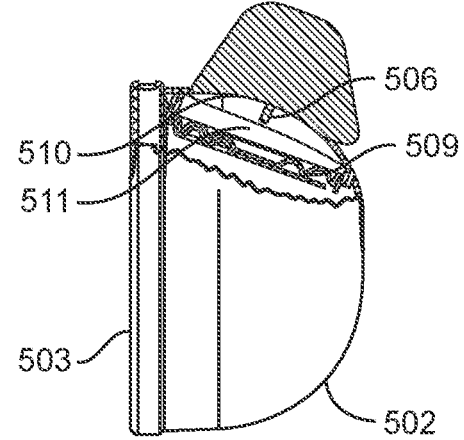
Figure 6C:
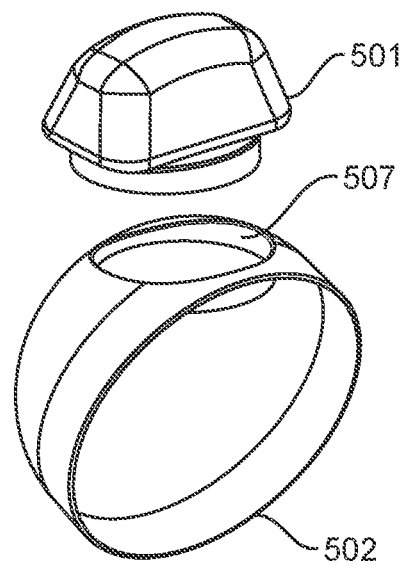

FIGS. 6A-6C illustrate a wearable breastmilk collection device 500 where the wearable breastmilk collection device 500 includes an external breast pump 501 that is removably attachable to a collection receptacle 502. In this instance the pump is connected directly to the vacuum reservoir 511 by the vacuum communication conduit 506. The collection device 500 is operated under variable suction parameters of vacuum by the external breast pump 501 and is connected to vacuum communication conduit 506 such that it provides suction to an vacuum reservoir 511. The vacuum reservoir 511 is created by pressing the external breast pump 501 into the pump connection cylinder and compressing the flexible diaphragm 509 to the half dome top 510.

Figure 7A:
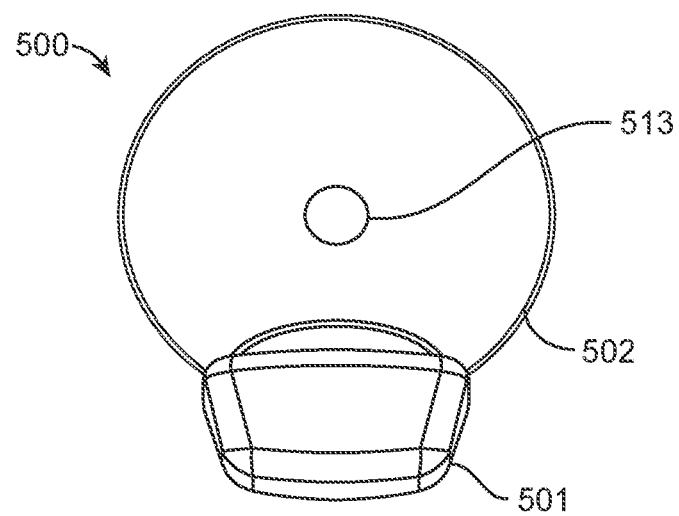
FIGS. 7A and 7B are top views of a breastmilk collection device with an electric pump, according to an alternative embodiment, illustrating operation of an optional light.

FIG. 7A illustrates a wearable breastmilk collection device 500 where the wearable breastmilk collection device 500 includes an external breast pump 501 that is located below the targeted nipple location 513, enabling visualization, supporting consistent nipple placement and overall proper use.

Figure 7B:
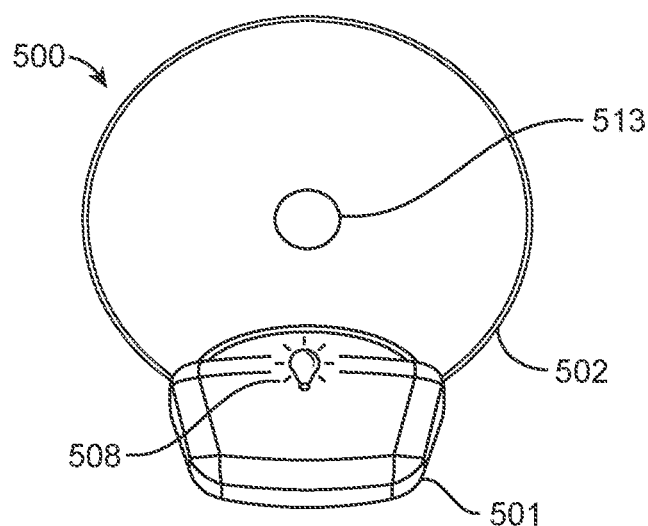

FIG. 7B illustrates a wearable breastmilk collection device 500 where the wearable breastmilk collection device 500 includes an external breast pump 501 that is located below the targeted nipple location 513 and a light 508 that can be switched on and off, facilitating visualization and supporting consistent nipple placement and overall proper use.

FIGS. 8A-8C illustrate a wearable breastmilk collection device 500 for collection of breastmilk from a mother by being placed in her brassier, such that when the device is in use the mother can be hands-free. The wearable breastmilk collection device 500 includes an internal breast pump 512 that is located within the collection receptacle 502, but not in direct communication or contact with the collected breastmilk. The internal breast pump 512 can be located in multiple different positions while still enabling better visualization and supporting consistent nipple placement and overall proper use.

FIG. 8D describes a wearable breastmilk collection device 500 where the wearable breastmilk collection device 500 includes an internal breast pump 512 such that a breast pump is an electromechanical device that generates a oscillating suction wave that is located below the targeted nipple location 513 and a light 508 that can be switched on and off enabling better visualization and supporting consistent nipple placement and overall proper use.

FIGS. 9A-9E illustrate another embodiment of a breastmilk collection system 600. The breastmilk collection system 600 includes a milk collection receptacle 601, a breast contacting flange 602, a flange receiver 603, a flexible diaphragm 604 and an adapter 605. The adapter 605 includes a flange attaching portion 610 for connecting to the breast contacting flange 602 and a receptacle attaching portion 622 for connecting to the collection receptacle 601. In some embodiments, the breastmilk collection system 600 may be provided without the collection receptacle 601, which may be sold separately. As best seen in the cross-section of FIG. 9D, the flange attaching portion 610 of the adapter 605 has a half-dome shape and includes a vacuum source attachment port 612, for connecting to one end of suction tubing connected to an electric breast pump (tubing and pump not shown). A space formed inside the half dome of the flange attaching portion 610, between its inner wall and the flexible diaphragm 604, acts as a vacuum reservoir 611, which is in fluid communication with the vacuum source attachment port 612. The flange receiver 603 is attached to the flange attaching portion 610 such that the flexible diaphragm 604 resides between the vacuum reservoir 611 and the flange receiver 603. As in previously described embodiments, the breast contacting flange 602 has a wide, breast accepting portion 602a and a narrow portion 602b attached to the flange receiver 603.

Figure 9D:
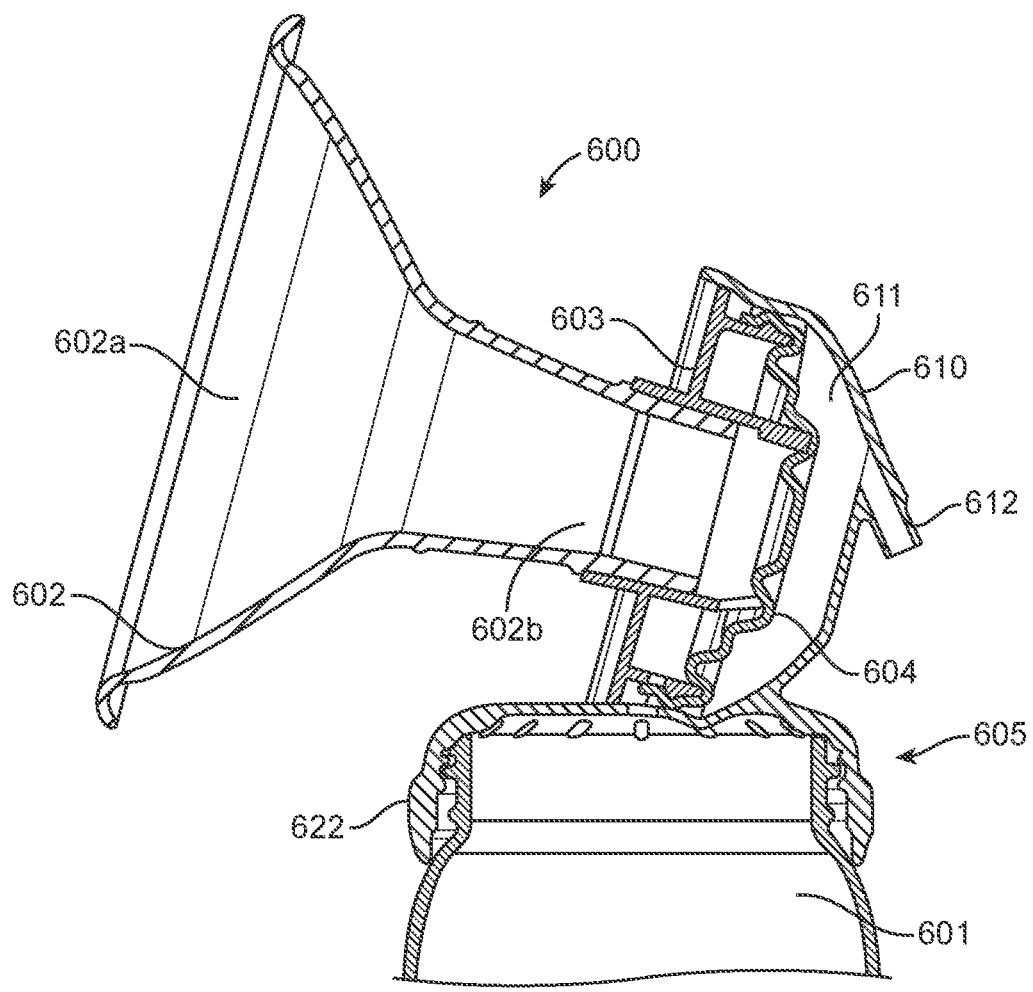
FIG. 9D is a close-up view of a portion of FIG. 9A.
Figure 9E:
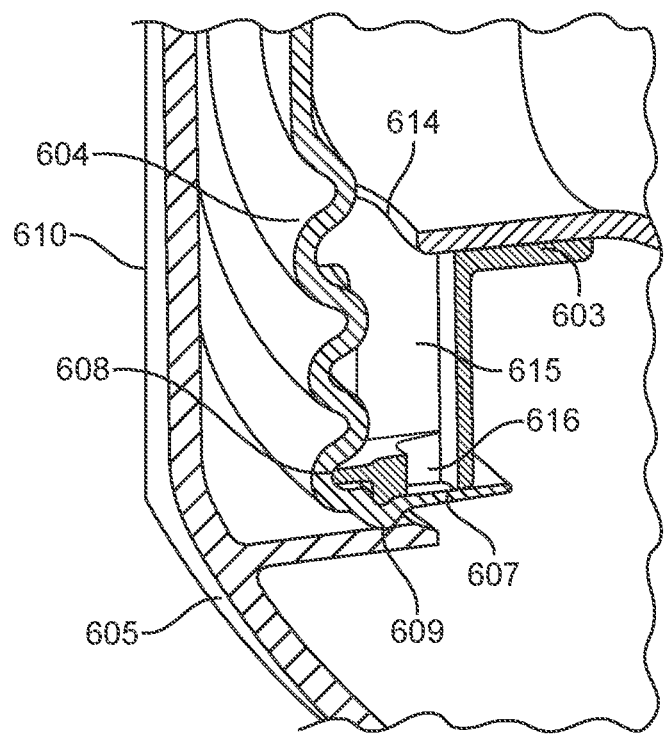
FIGS. 9E and 9F are close-up views of another portion of the breastmilk collection device of FIGS. 9A-9D, illustrating a path for milk flow through the device.
Figure 9F:
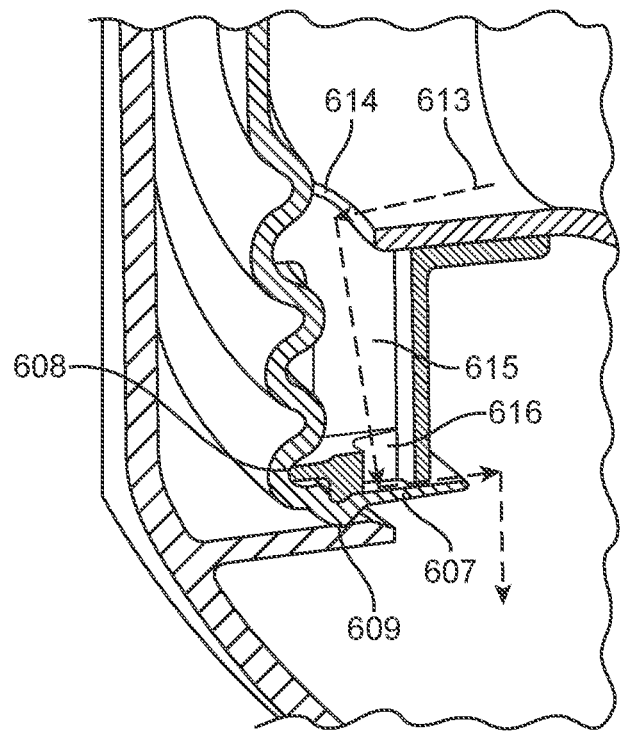

Referring to FIGS. 9E and 9F, the flexible diaphragm 604 includes an integrated one-way valve 607, similar to the one-way valve described in relation to FIGS. 4C and 4D. The flexible diaphragm 604 is located between, and directly connected to, the flange receiver 603 and the flange attaching portion 610 of the adapter 605. This connection creates both an inner seal 608 and outer seal 609. As mentioned above, the flexible diaphragm 604 is captured between the flange receiver 603 and the flange attaching portion 610, thus forming the vacuum reservoir 611. The vacuum reservoir 611 is created by compressing the flange receiver 603 against the flexible diaphragm 604 and the adapter 605.

The breastmilk collection system 600 operates under variable suction parameters of vacuum via the vacuum source attachment port 612 that provides suction to the vacuum reservoir 611. Suction force is transmitted from the vacuum reservoir 611 to the breast contacting flange 602 via the flexible diaphragm 604. Vacuum force is actuated from the flexible diaphragm 604 in cycles, which helps extract milk or colostrum from the breast and allows the milk or colostrum to flow into the collection receptacle 601 anterior to the one-way valve 607. A flow path 613 from the breast contacting flange 602 to the collection receptacle 601 includes a flow entrance 614, located at the distal end of the breast contacting flange 602, a flow chamber 615 and a flow exit 616.

Figure 9G:
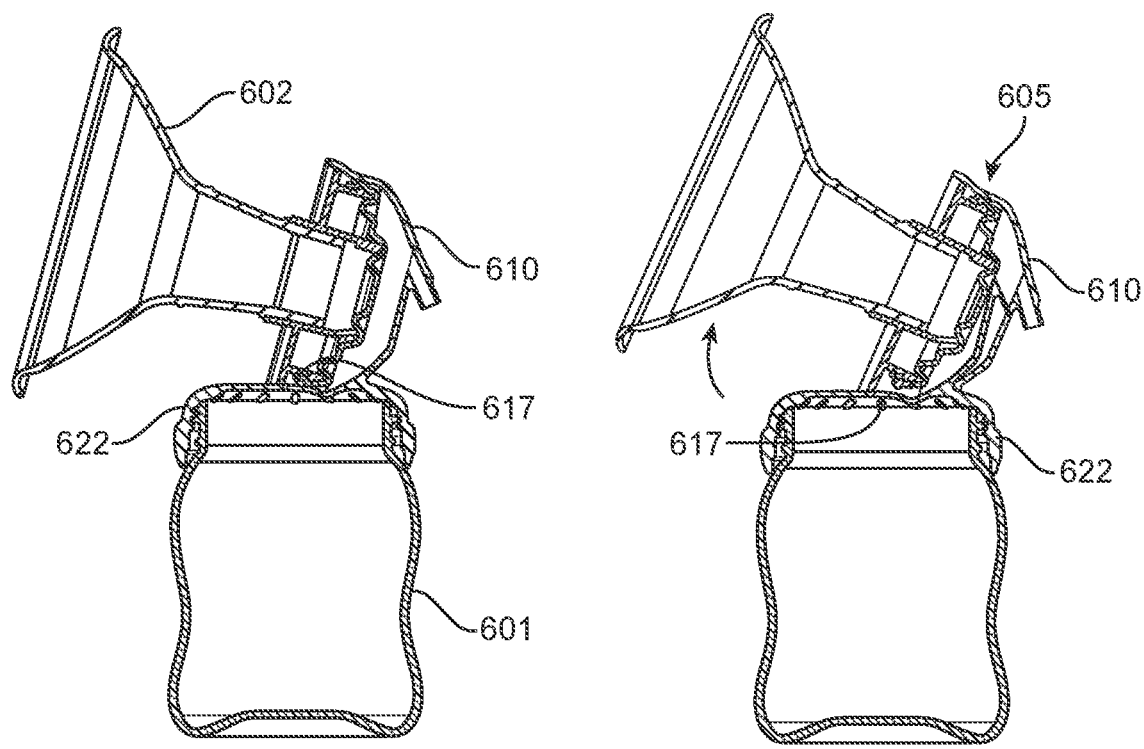
FIG. 9G is a side, cross-sectional view of the breastmilk collection device of FIGS. 9A-9F, illustrating the ability of a portion of the device to tilt.
Figure 9H:
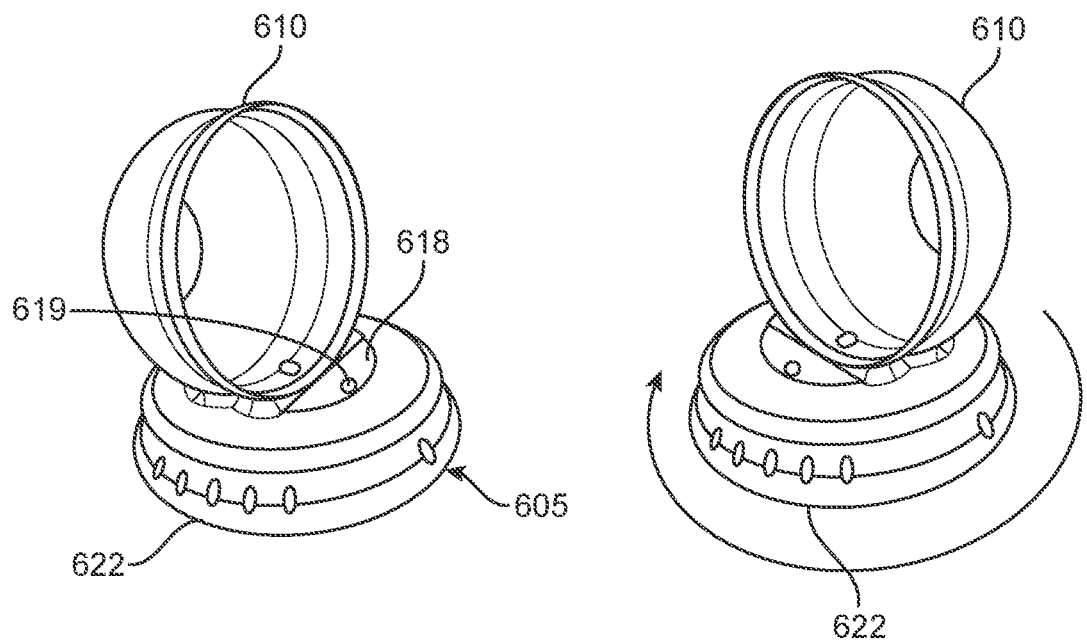
FIG. 9H is two perspective views of a top portion of the breastmilk collection device of FIGS. 9A-9G, illustrating the ability of a portion of the device to rotate.

Referring now to FIGS. 9G and 9H, in some embodiments, the adapter 605 may include one or more adjustment features, for example to allow adjustment of the flange attaching portion 610 relative to the receptacle attaching portion 622. This adjustability may facilitate a more comfortable pumping position for the woman using the system 600. FIG. 9G illustrates a tilting mechanism 617 that allows the user to tilt the flange attaching portion 610 relative to the receptacle attaching portion 622 and thus change the angle of the breast contacting flange 602 angle relative to the collection receptacle 601. FIG. 9H illustrates a rotation mechanism 618 that allows the user to rotate the flange attaching portion 610 relative to the receptacle attaching portion 622. An optional bottle vent hole 619 on the top of the receptacle attaching portion 622 is also shown—it allows air displaced by the movement of milk or colostrum into the collection receptacle 601 to be vented.

Figure 10A:
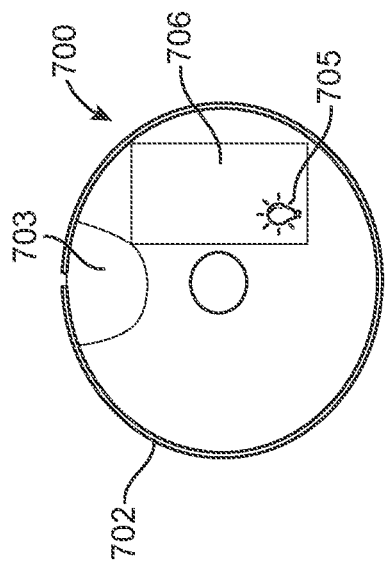
FIGS. 10A-10C are side/cross-sectional, front and rear views, respectively, of a wearable breast milk collection device, according to one embodiment.
Figure 10B:
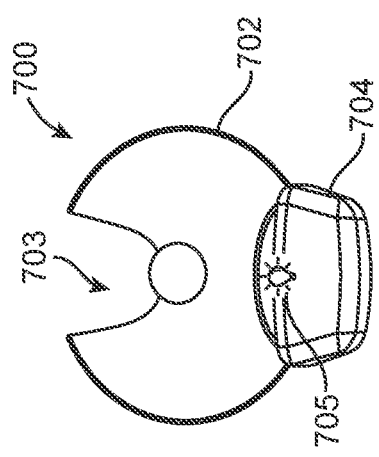
Figure 10C:
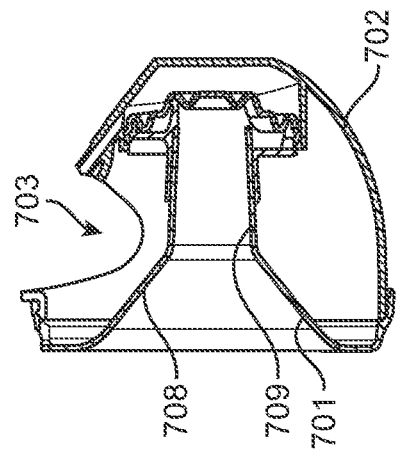

FIGS. 10A-10C illustrate another alternative embodiment of a wearable collection cup 700 for collection of breastmilk from a mother. This embodiment may include all of the components described for embodiments above, such as a flexible diaphragm, a flange receiver and a vacuum reservoir, although not all features are labeled. In this embodiment, the wearable collection cup 700 includes either an external breast pump 704 (FIG. 10B, shown with optional light 705) that is attachable to a collection receptacle 702 or an internal breast pump 706 (FIG. 10C). The collection receptacle 702 has a visualization recess 703 that comes in close proximity to the area where the wide portion 708 of the breast contacting flange 701 intersects with the narrow portion 709. The visualization recess 703 is located on the upper, outer portion of the collection receptacle 702, enabling better visualization and supporting consistent nipple placement and overall proper use.

Figure 11A:
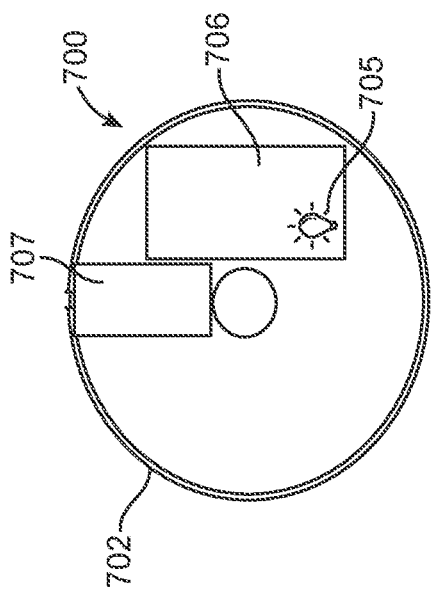
FIGS. 11A-11C are side/cross-sectional, front and rear views, respectively, of a wearable breast milk collection device, according to an alternative embodiment.
Figure 11B:
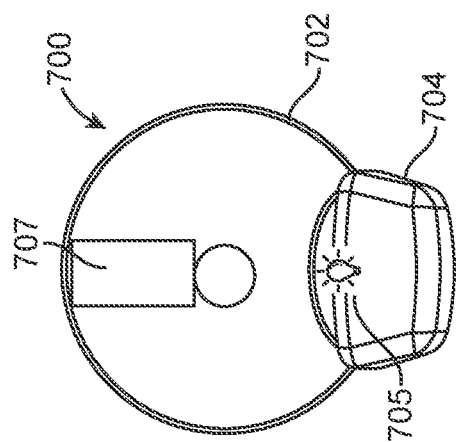
Figure 11C:
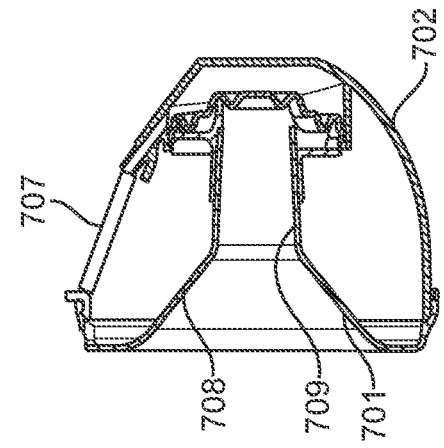

FIGS. 11D-11F illustrate another alternative embodiment of a wearable collection cup 700 for collection of breastmilk from a mother. The wearable collection cup 700 contains either an external breast pump 704 and light 705 that is attachable to a collection receptacle 702 or an internal breast pump 706 and light 705. The collection receptacle 702 has a visualization lens 707 located in the upper portion of the collection receptacle 702. The visualization lens could be molded into the collection receptacle or could be a separate component that is joined to the collection receptacle 702. The visualization lens 703 is located on the upper, outer portion of the collection receptacle 702 enabling better visualization and supporting consistent nipple placement and overall proper use.

Figure 12:
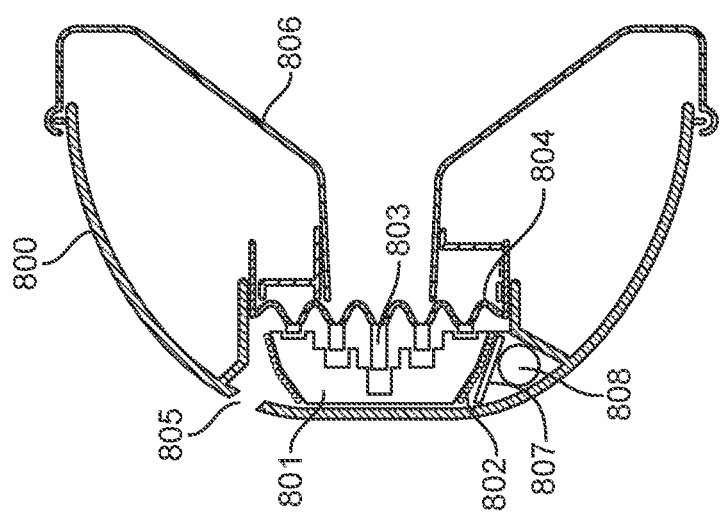
FIG. 12 is a side, cross-sectional view of a wearable breastmilk collection device with a built-in pump and driven by electromechanical actuation of components, according to one embodiment.

Referring now to FIG. 12, in another alternative embodiment, a wearable breastmilk collection device 800 has an integrated breast pump, including a solenoid coil 802, with a magnetic core 801, such as soft iron, to concentrate a magnetic field, and an armature 803, also made of a magnetic core or magnet integrated into a diaphragm 804. When current is passed through the coil 802, a magnetic field is created, which is concentrated into the magnetic core 801. This will attract the armature 803, thus pulling the diaphragm 804 in, creating a vacuum in a breast contacting flange 806. A vent hole 805 helps equalize pressure across the device when the solenoid is on. When current is turned off, the diaphragm 804 acts as a spring to return the armature 803 back to initial position, thus releasing the pressure within the flange 806 without the use of another solenoid as in a typical breast pump. A printed circuit board (PCB) 807 (including a control unit) and a battery 808 are used to control and power the breast pump. In an alternative embodiment, the armature 803 is not embedded into the diaphragm, but rather may be attached to a piston.

Figure 13:
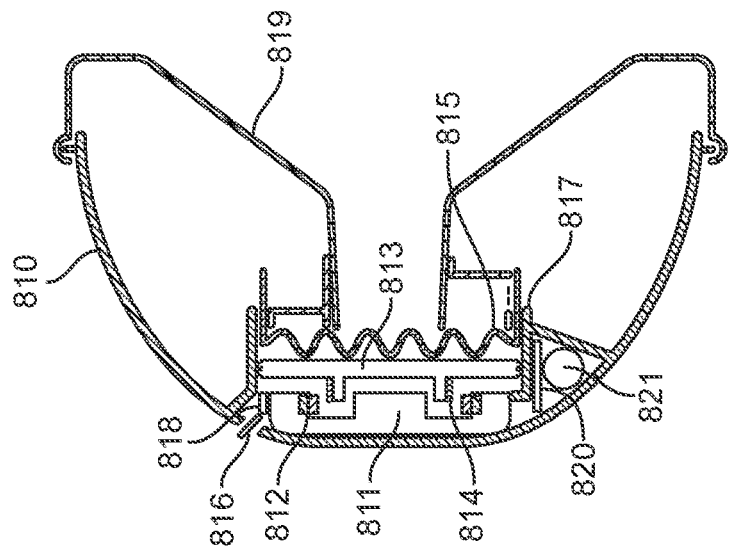
FIG. 13 is a side, cross-sectional view of a wearable breastmilk collection device with a built-in pump and driven by electromechanical actuation of components, according to an alternative embodiment.

Referring now to FIG. 13, an alternative embodiment of a wearable breastmilk collection device 810 with an integrated breast pump is illustrated. In various embodiments, the integrated breast pump may include a linear actuator, such as a voice coil actuator, moving magnet actuator or moving coil actuator. The breastmilk collection device 810 of FIG. 13 includes a moving coil actuator. The moving coil actuator includes a yoke 811 made of magnetic core, with a permanent magnet 812 attached. A bobbin 813 (or "coil holder") has a wire coil 814 wound around it, and the bobbin 813 acts as a piston with rubber gasket 817 to ensure an air-tight seal. As current passes through the wire coil 814, a lateral force is created, which drives the bobbin 813 (piston) left and right. As the bobbin 813 moves left and right, because of the air-tight seal, a diaphragm 815 moves along with it, thus generating a vacuum force on a breast contacting flange 819. A vent hole 816 helps equalize pressure when the bobbin 813 moves back and forth. A sensor 818, such as a hall-effect sensor or pressure sensor, can provide feedback resulting in the bobbin 813 operating in a closed-feedback loop. This allows for precise control of the vacuum created in the flange 819. The precise control of the piston/bobbin movement also allows the breast pump to create micro-vibrations in the vacuum waveform to aid letdown. To release the vacuum in the flange 819, the current is reversed, causing the bobbin 813 to move in the opposite direction, thus releasing the vacuum in the flange 819. A PCB 820 (including a control unit) and a battery 821 are included to control and power the breast pump. This design also does not require an additional solenoid, as required in a traditional breast pump design. In an alternative embodiment, the bobbin 813 does not need to be a separate component. The wire coil 814 can be embedded into the diaphragm 815, similar to the diaphragm 804 of the previously described embodiment.

Figure 14:
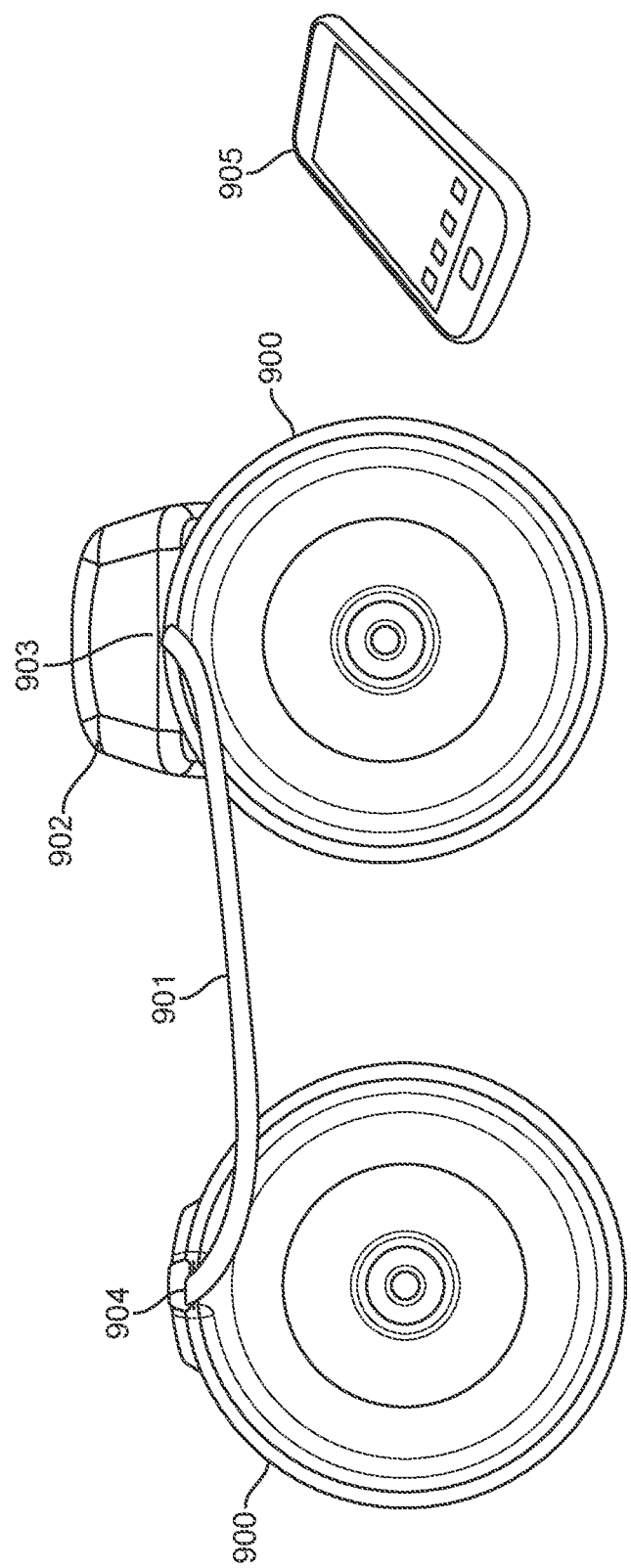
FIG. 14 is a front facing view of a wearable breastmilk collection system for double pumping, including a pump directly attached to one breastmilk collection device and indirectly to a second collection device via a suction connection tube.

FIG. 14 illustrates a breastmilk collection system that includes two breastmilk collection devices 900 collecting milk from both breasts simultaneously or sequentially. In this system, either cup 900 can be interchangeably or uniquely detached or attached to a source of suction, such as an electromechanical vacuum pump 902, which may include components such as a PCBA, vacuum motor, battery, and/or other components such as buttons, Bluetooth antennas or other signaling systems, LCD or other display, or other mechanisms such as would be needed for a user to operate the system including a button or feature that enables the user to pump left side only, right side only, or both sides simultaneously with or without a time out feature such as a sleep timer. One vacuum pump system 902 is connected to a first collection cup 900 via a connection in the base or side of the vacuum pump system 902 and to a second collection cup 900 via a connector tubing 901 that spans at least the distance between each of the cups if placed inside a brassier in operation. The connector tubing 901 connects the vacuum pump system 902 to the second cup 900 via a connector port 904 on the second cup 900, which transmits suction from the vacuum pump system 902 to the second collection cup 900. The pump 902 may also be wirelessly, NFC, RF, or Bluetooth connected or other signal service connected, such as but not limited to 3G or 4G to a mobile device or a additional remote control 905.

Figure 17:
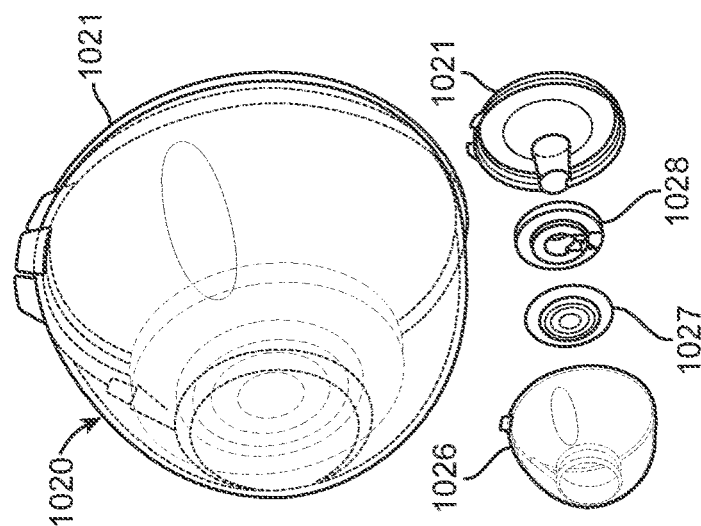
FIG. 17 is a perspective and exploded view of a wearable breastmilk collection device with a flexible diaphragm, according to another alternative embodiment.
Figure 16:
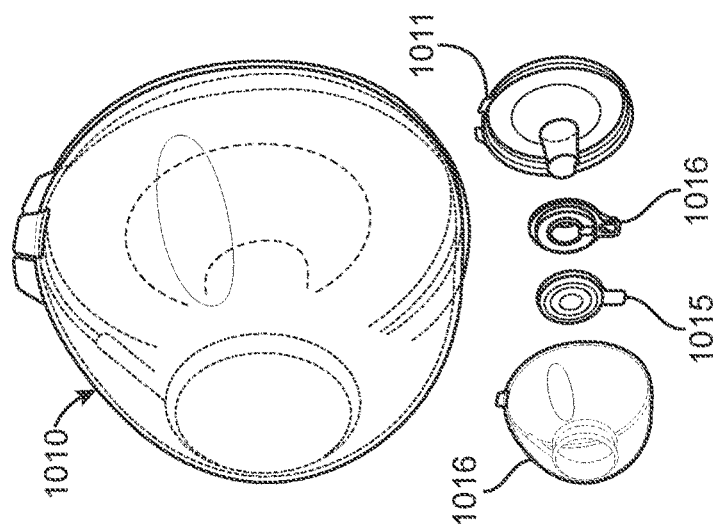
FIG. 16 is a perspective and exploded view of a wearable breastmilk collection device with a flexible diaphragm with a tab, according to an alternative embodiment.
Figure 15:
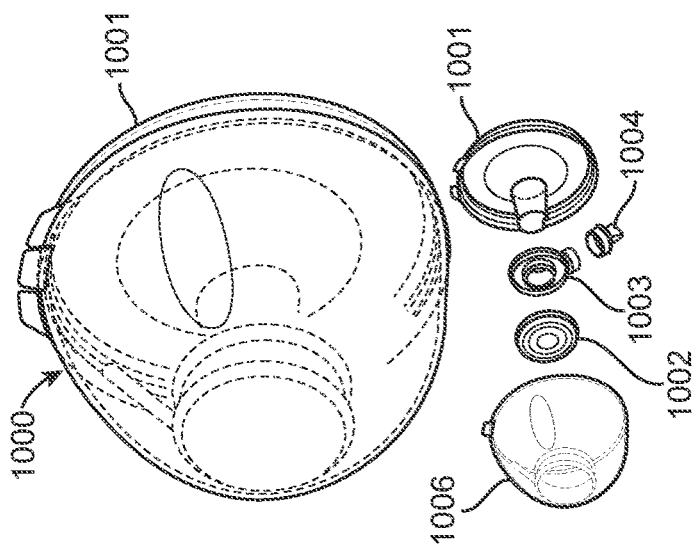
FIG. 15 is a perspective and exploded view of a wearable breastmilk collection device with a flexible diaphragm and a duckbill valve, according to one embodiment.

FIGS. 15-17 illustrate three exemplary embodiments of wearable breastmilk collection devices 1000, 1010, 1020, each of which includes a cup 1006, 1016, 1026 (or "milk collection receptacle") and a breast accepting flange 1001, 1011, 1021. In each embodiment, a wide open end of the cup 1006, 1016, 1026 attaches to a wide portion of the breast accepting flange 1001, 1011, 1021 to form an inner compartment for storage of milk and/or colostrum expressed from the breast. In the embodiment of FIG. 15, an internal valve system of the wearable breastmilk collection device 1000 includes a flange receiver 1003, a duckbill valve 1004 and a pressure communicating flexible diaphragm 1002. In the embodiment of FIG. 16, an internal valve system of the wearable breastmilk collection device 1010 includes an integrated pressure communicating flexible diaphragm 1015 with a bill flap and a flange receiver 1016 with a milk flow channel that leads from the breast contacting flange 1011 into the storage compartment within the cup 1016. In the embodiment of FIG. 17, an internal valve system includes an integrated pressure communicating flexible diaphragm 1027 and a flange receiver 1028 with a milk flow channel that leads from the breast contacting flange 1021 into the storage compartment within the cup 1026. In this embodiment, the flexible diaphragm 1027 has a rim with a uniform shape that eliminates orientation specific assembly.

FIGS. 18A-18D illustrate another embodiment of a breastmilk collection device 1700. In this embodiment, the collection device 1700 is handheld and uses a manual pumping mechanism rather than a motorized pump. The breastmilk collection device 1700 includes a breast contacting flange 1702, a flexible diaphragm 1704, a pull rod 1706, a handle 1712, an adaptor, and a milk bottle 1718 (or "milk collection receptacle"). The adapter 1716 includes a flange attaching portion 1719 and a receptacle attaching portion 1720, and it houses a flange receiver 1717 and the flexible diaphragm 1704. The narrow end of the breast contacting flange 1702 attaches to the flange receiver 1717, and the diaphragm 1704 attaches to an opposite side of the flange receiver 1717. The adapter 1716 connects via the bottle connector 1720 to the milk bottle 1718. Inside the adapter 1716, the flexible diaphragm 1704 includes an opening through which the pull rod 1706 extends and is attached. The pull rod 1706 includes a proximal bulb 1708 and a distal bulb 1710. The flange attaching portion 1719 of the adapter 1716, along with the flexible diaphragm 1704, form a vacuum reservoir 1715.

Figure 18A:
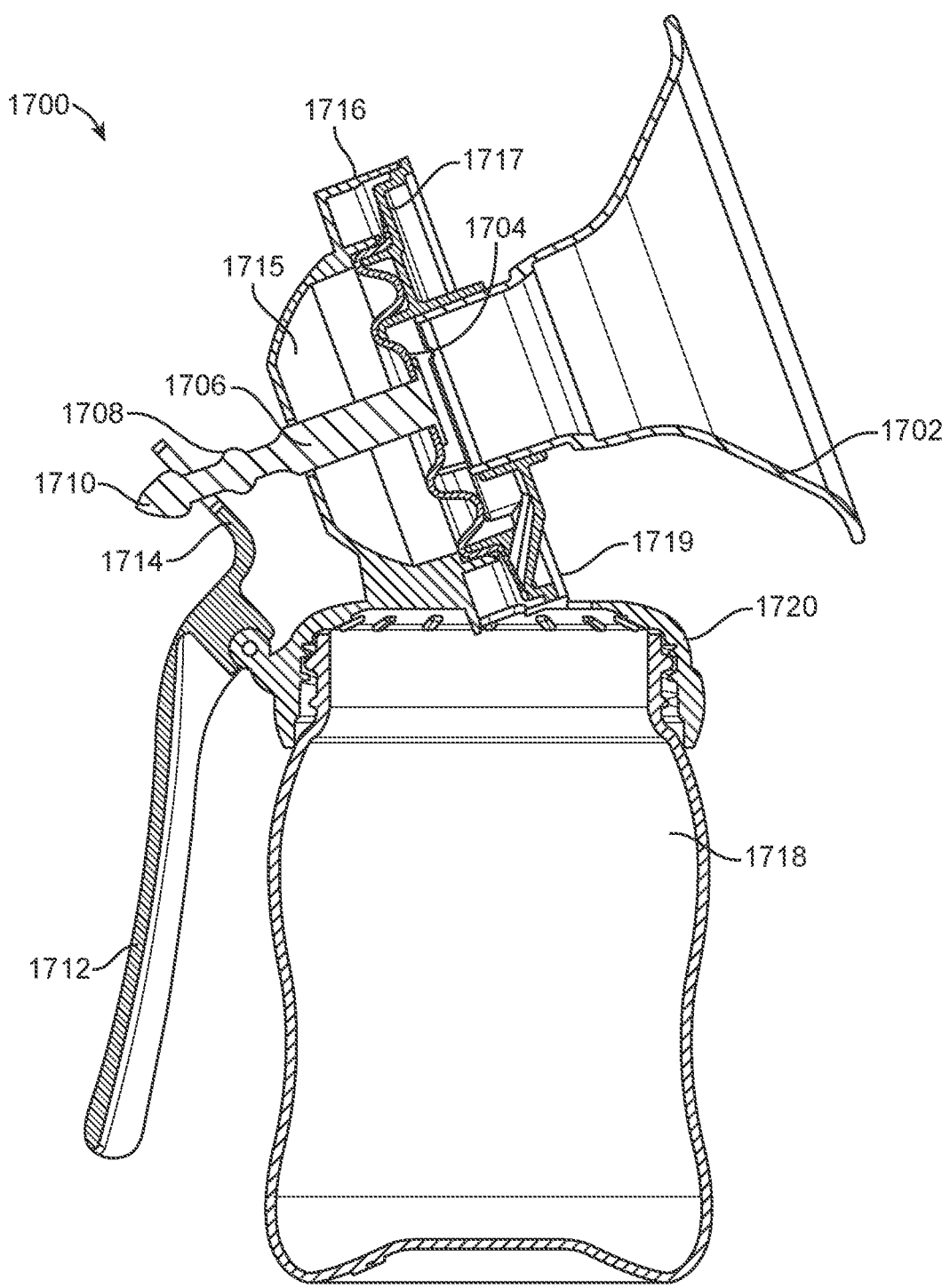
FIGS. 18A-18D are side/cross-sectional, partial rear, side and partial perspective views, respectively, of a manual breastmilk collection device with a handle, according to one embodiment.
Figure 18B:
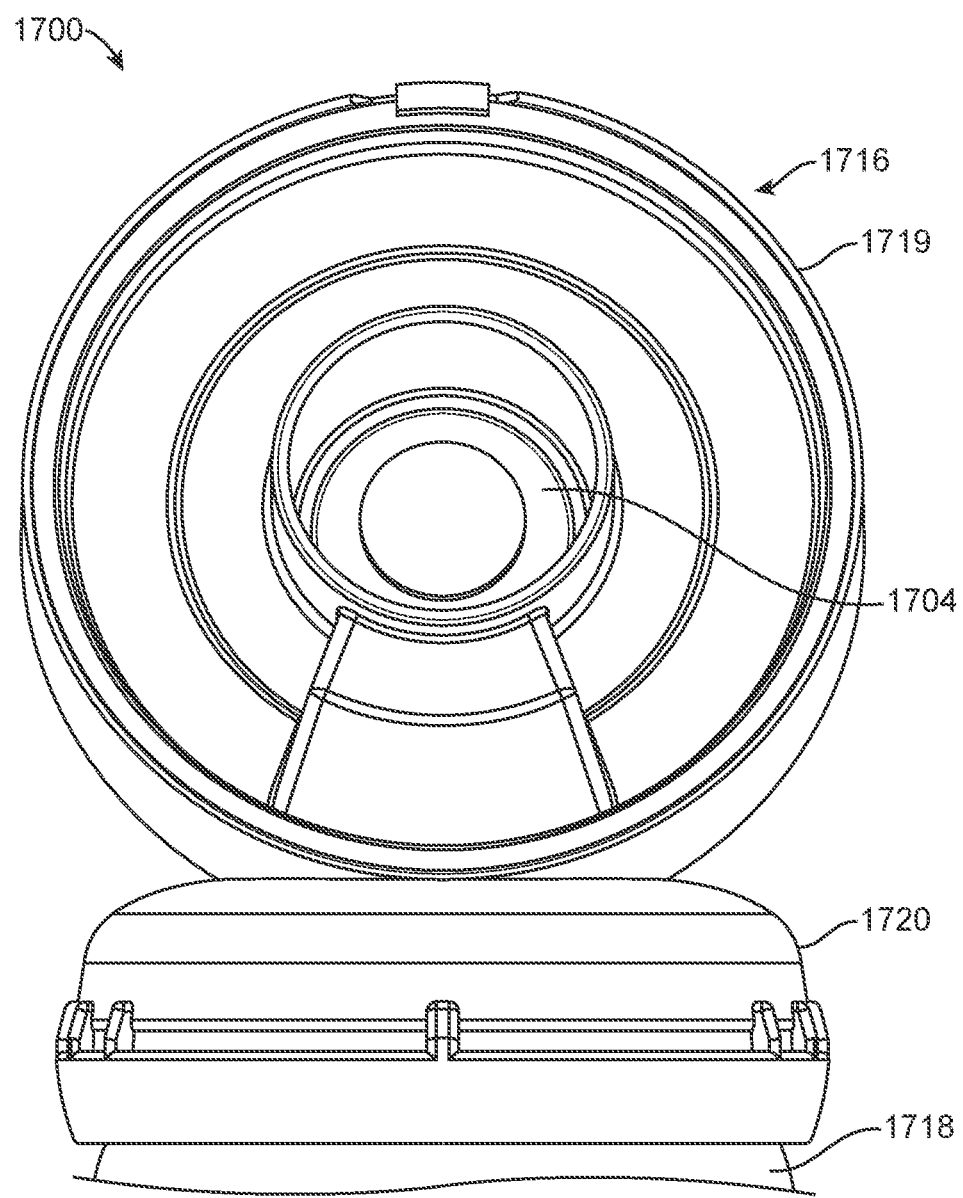
Figure 18C:
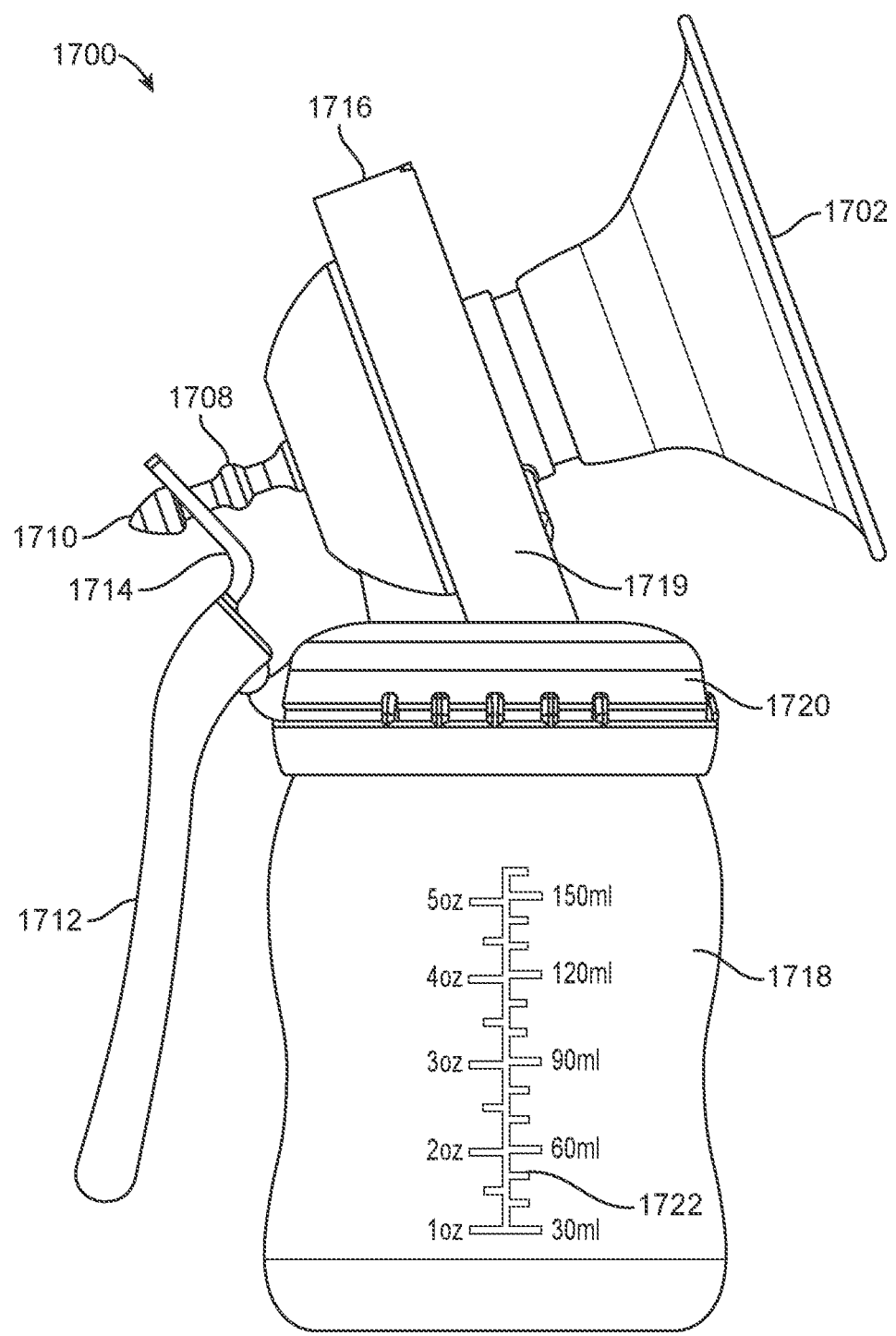
Figure 18D:
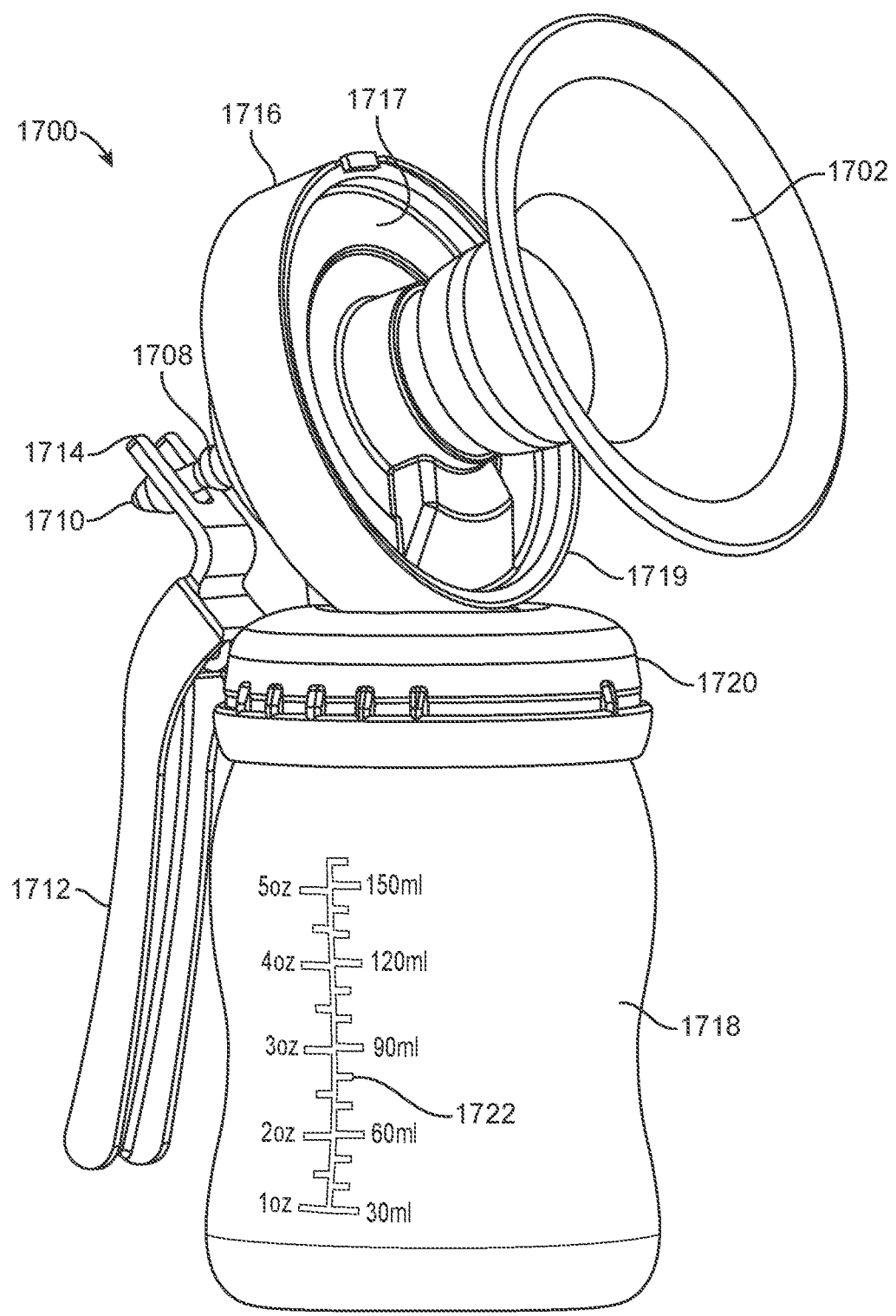

A handle attachment portion 1714 is clamped over the pull rod and may be moved from the position shown in FIG. 18A, where it resides between the proximal bulb 1708 and the distal bulb 1710, to a location on the other side of the proximal bulb 1708 (to the right in FIG. 18A). The attachment of the handle attachment portion 1714 to the pull rod 1706 can best be seen in FIG. 18D. In this embodiment, the handle attachment portion 1714 includes a slot into which the pull rod 1706 fits. The illustrated position of the handle attachment portion 1714 on the pull rod 1706 may be used to create shorter pulls on the diaphragm 1704, for example for stimulation of the breast, while the position farther to the right (farther proximally) along the pull rod 1706 may be used to create larger pulls on the diaphragm 1704, for example for milk expression. In use, the woman presses the handle 1712 toward the bottle 1718, thus causing the pull rod 1706 to pull on the diaphragm 1704, which causes a suction force on the breast via the breast contacting flange 1702. As shown in FIGS. 18C and 18D, the bottle 1718 may optionally include fluid level markings 1722.

As with previously described embodiments, the flexible diaphragm 1704 forms a one-way valve with the flange receiver 1717. The one-way valve allows expressed milk and/or colostrum to flow out of the narrow end of the breast contacting flange 1702 and into the milk bottle 1718 when suction is applied, and then closes when suction is removed.

The above is meant to be a complete and accurate description of the invention. The description provides examples, however, and these examples are not meant to be exhaustive. Alterations may be made to any of the embodiments described above, without departing from the scope of the invention described by the claims below.

The invention claimed is:

1. A breastmilk collection device, comprising:
a breast contacting flange having a wide portion for accepting a breast and a narrow portion;
a vacuum reservoir;
a milk container; and
a single flexible diaphragm, with a planar sealing surface extending along an entire circumference of the single flexible diaphragm, separating the narrow portion of the breast contacting flange from the vacuum reservoir and the milk container;
wherein the single flexible diaphragm is positioned in a sealed configuration, in which the breast contacting flange is sealed off from the vacuum reservoir, and
wherein the single flexible diaphragm acts as a one-way valve with a portion of the circumference of the single flexible diaphragm unsealing to allow expressed milk to flow through a milk flow opening into the milk container when an opening pressure is reached in the breast contacting flange.

2. The breastmilk collection device of claim 1, further comprising a cup attached to the wide portion of the breast contacting flange, wherein the cup comprises:
a first portion that forms the milk container; and
a second portion that forms the vacuum reservoir.

3. The breastmilk collection device of claim 2, wherein the cup further comprises a suction tube attachment port in fluid communication with the vacuum reservoir.

4. The breastmilk collection device of claim 2, further comprising measurement lines on the cup to measure milk stored in the milk container.

5. The breastmilk collection device of claim 2, further comprising a breast pump attached to the cup.

6. The breastmilk collection device of claim 5, wherein the breast pump is removably attached to the cup.

7. The breastmilk collection device of claim 5, wherein the breast pump is located inside the milk container and comprises:
a printed circuit board; and
a power source.

8. The breastmilk collection device of claim 5, further comprising tubing for connecting the breast pump to an additional breastmilk collection device, such that the breastmilk collection device and the additional breastmilk collection device can be worn at a same time and used simultaneously or sequentially.

9. The breastmilk collection device of claim 1, further comprising an adapter attached to the narrow portion of the breast contacting flange, wherein the adapter forms the vacuum reservoir and houses the single flexible diaphragm.

10. The breastmilk collection device of claim 9, wherein the adapter comprises a suction tube attachment port in fluid communication with the vacuum reservoir.

11. The breastmilk collection device of claim 9, wherein the adapter comprises a milk container attachment portion for attaching to the milk container.

12. The breastmilk collection device of claim 11, wherein a flange connecting portion of the adapter is configured to move by at least one of tilting or rotating relative to the milk container attachment portion.

13. The breastmilk collection device of claim 9, further comprising:
a pull rod attached to the single flexible diaphragm and extending out of an opening on a back of the adapter; and
a handle attached to the adapter and the pull rod for pulling back on the pull rod to manually pull on the single flexible diaphragm to generate vacuum force.

14. The breastmilk collection device of claim 13, wherein the pull rod comprises two settings defining two different locations for attachment of the handle to the pull rod, to generate at least two different amounts of pulling force on the single flexible diaphragm.

15. A method of expressing and collecting breastmilk from a breast, the method comprising:
positioning a breastmilk collection device on the breast, wherein the breastmilk collection device comprises:
a breast contacting flange having a wide portion for accepting the breast and a narrow portion;
a vacuum reservoir;
a milk container;
a flexible diaphragm separating the narrow portion of the breast contacting flange and the vacuum reservoir; and
wherein the flexible diaphragm is positioned in a sealed configuration in a first sealing plane, in which the breast contacting flange is sealed off from the vacuum reservoir, and
wherein the flexible diaphragm acts as a one-way valve within a second sealing plane parallel to the first sealing place to allow expressed milk to flow through a milk flow opening into the milk container; and
expressing breastmilk from the breast, using the breastmilk collection device.

16. The method of claim 15, wherein positioning the breastmilk collection device on the breast comprises positioning the breastmilk collection device inside of a brassiere.

17. The method of claim 16, further comprising attaching the breastmilk collection device to a pump located outside of the brassiere.

18. The method of claim 17, wherein attaching the breastmilk collection device to the pump comprises attaching tubing from the pump to a vacuum source attachment port of the breastmilk collection device that is in fluid communication with the vacuum reservoir.

19. The method of claim 16, further comprising attaching the breastmilk collection device to a pump located inside the brassiere.

20. The method of claim 15, wherein expressing breastmilk from the breast comprises squeezing a handle of the breastmilk collection device.

21. The method of claim 20, further comprising adjusting a position of an attachment point of the handle to a pull rod of the breastmilk collection device to change an amount of pulling force generated on the flexible diaphragm by the handle.

22. The method of claim 15, further comprising attaching the breastmilk collection device to an electric pump to express the breastmilk.

23. The method of claim 15, further comprising attaching the milk container to the breastmilk collection device to collect the expressed breastmilk.

* * * * *